(12) United States Patent
Polwart et al.

(10) Patent No.: US 8,124,029 B2
(45) Date of Patent: Feb. 28, 2012

(54) APPARATUS AND METHODS FOR MICROFLUIDIC APPLICATIONS

(75) Inventors: Stuart Polwart, Stirlingshire (GB); Joel Fearnley, Peeblesshire (GB); Douglas Roy, Edinburgh (GB); Peter Ghazal, Edinburgh (GB)

(73) Assignee: LAB901 Limited, Midlothian (GB)

( * ) Notice: Subject to any disclaimer, the term of this patent is extended or adjusted under 35 U.S.C. 154(b) by 1168 days.

(21) Appl. No.: 10/496,741

(22) PCT Filed: Nov. 27, 2002

(86) PCT No.: PCT/GB02/05367
§ 371 (c)(1),
(2), (4) Date: Dec. 9, 2004

(87) PCT Pub. No.: WO03/045557
PCT Pub. Date: Jun. 5, 2003

(65) Prior Publication Data
US 2005/0089449 A1  Apr. 28, 2005

(30) Foreign Application Priority Data
Nov. 27, 2001 (GB) .................... 0128350.6

(51) Int. Cl.
*B01L 3/00* (2006.01)
(52) U.S. Cl. ...................................... 422/502
(58) Field of Classification Search .............. 422/502
See application file for complete search history.

(56) References Cited

U.S. PATENT DOCUMENTS

| | | | |
|---|---|---|---|
| 4,049,147 A | 9/1977 | Stiles et al. | |
| 4,065,263 A | 12/1977 | Woodbridge, III | |
| 4,247,591 A | 1/1981 | Gould | |
| 4,472,471 A | 9/1984 | Klein et al. | |
| 5,284,570 A | 2/1994 | Savage et al. | |
| 5,288,463 A | 2/1994 | Chemelli | |
| 5,500,071 A | 3/1996 | Kaltenbach et al. | |
| 5,658,647 A | 8/1997 | Magill et al. | |
| 5,665,469 A | 9/1997 | Brandt et al. | |
| 5,882,571 A | 3/1999 | Kaltenbach et al. | |
| 5,932,799 A | 8/1999 | Moles | |
| 6,054,100 A | 4/2000 | StanchField | |
| 6,103,199 A * | 8/2000 | Bjornson et al. | 422/100 |
| 6,123,798 A * | 9/2000 | Gandhi et al. | 156/292 |
| 6,284,113 B1 * | 9/2001 | Bjornson et al. | 204/453 |

(Continued)

FOREIGN PATENT DOCUMENTS
EP 0 976 453 2/2000
(Continued)

OTHER PUBLICATIONS

Byung-Ho, et al., "Fabrication of three-dimensional microfluidic systems by stacking molded polydimeethylsiloxane(PDMS) layers" *Proceedings of the SPIE*, SPIE, Bellingham, VA, U.S., vol. 3877, pp. 222-229.

(Continued)

*Primary Examiner* — Lore Jarrett

(57) ABSTRACT

Non-rigid tape apparatus and fabrication methods for microfluidic processing applications such as gel electrophoresis are provided, where microfluidic processing is performed on selected areas. Parts of the tape are formed by high pressure plastic film forming. Membranes and other structures are self sealing during and after penetration by pipettes and electrical probes. Rigid exoskeleton elements protect the non-rigid parts during processing and facilitate transport of the tape.

21 Claims, 21 Drawing Sheets

U.S. PATENT DOCUMENTS

| | | | |
|---|---|---|---|
| 6,627,159 B1 * | 9/2003 | Bedingham et al. | 422/100 |
| 6,632,653 B1 * | 10/2003 | Astle | 435/287.2 |
| 6,803,019 B1 | 10/2004 | Bjornson et al. | |
| 6,863,878 B2 * | 3/2005 | Klepper | 423/650 |
| 6,960,467 B2 * | 11/2005 | Shieh et al. | 435/287.2 |
| 7,155,344 B1 | 12/2006 | Parce et al. | |
| 2001/0005489 A1 | 6/2001 | Roach et al. | |
| 2001/0020588 A1 | 9/2001 | Adocrian et al. | |
| 2001/0029983 A1 | 10/2001 | Chou et al. | |
| 2001/0055812 A1 * | 12/2001 | Mian et al. | 436/45 |
| 2003/0017467 A1 | 1/2003 | Hooper et al. | |
| 2004/0101442 A1 | 5/2004 | Frechet et al. | |
| 2005/0089449 A1 | 4/2005 | Polwart et al. | |
| 2009/0022628 A1 * | 1/2009 | Polwart et al. | 422/82.02 |

FOREIGN PATENT DOCUMENTS

| | | |
|---|---|---|
| EP | 1388369 | 2/2004 |
| WO | WO 94 26414 | 11/1994 |
| WO | WO 97 47967 | 12/1997 |
| WO | WO9919717 * | 10/1998 |
| WO | WO 99 03584 | 1/1999 |
| WO | WO 99 19717 | 4/1999 |
| WO | WO 99 43432 | 9/1999 |
| WO | WO 99/65664 A1 | 12/1999 |
| WO | WO 01 07892 | 2/2001 |
| WO | WO 01 26812 | 4/2001 |
| WO | WO 01 30490 | 5/2001 |
| WO | WO 01 54814 | 8/2001 |
| WO | WO 02/081934 A2 | 10/2002 |
| WO | WO 03/045557 | 6/2003 |
| WO | WO 2004/071660 | 8/2004 |
| WO | WO 2004/080597 A2 | 9/2004 |

OTHER PUBLICATIONS

Khoo, et al., "Micro magnetic silicone elastomer membrane actuator" *Sensors and Actuators*, Elsevier Sequoia SA, Lausanne.

International Search Report issued in Application No. PCT/GB2002/05339, dated Aug. 18, 2003.

International Search Report issued in Application No. PCT/GB2002/05367, dated Oct. 14, 2003.

International Search Report issued in Application No. PCT/GB2006/000444, dated Sep. 11, 2006.

* cited by examiner

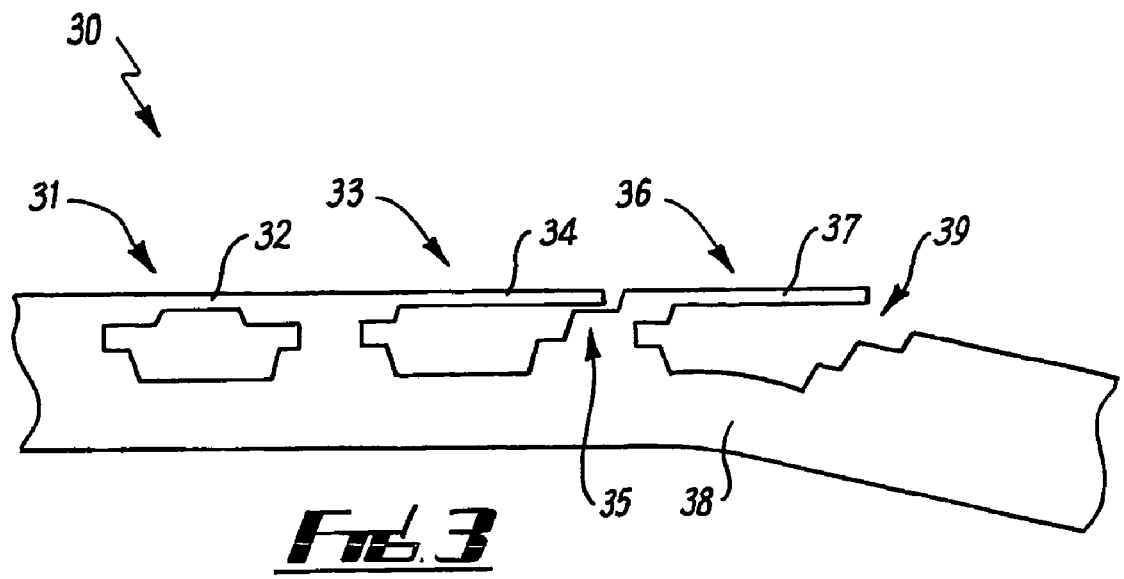
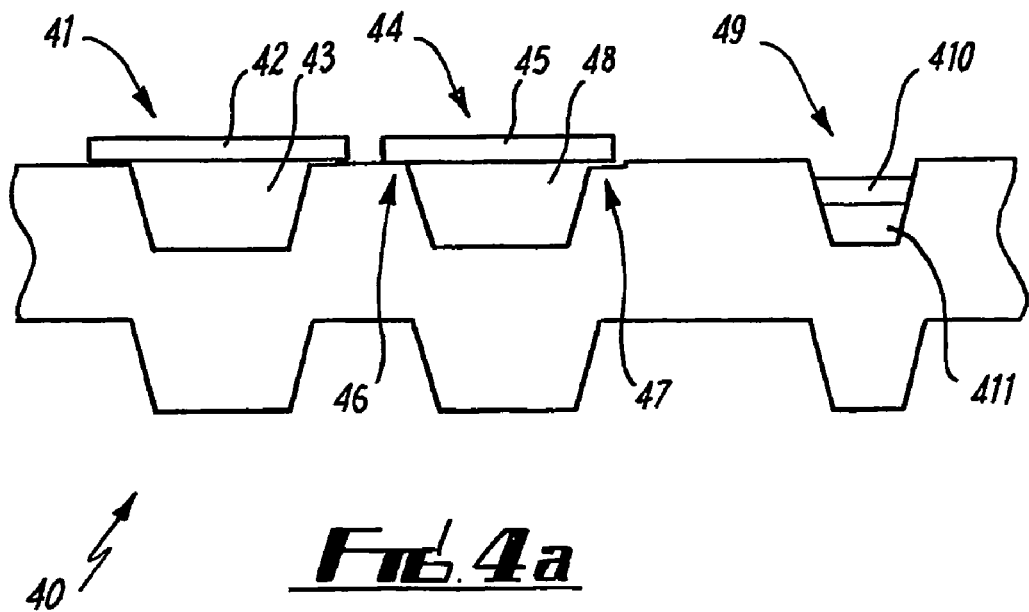

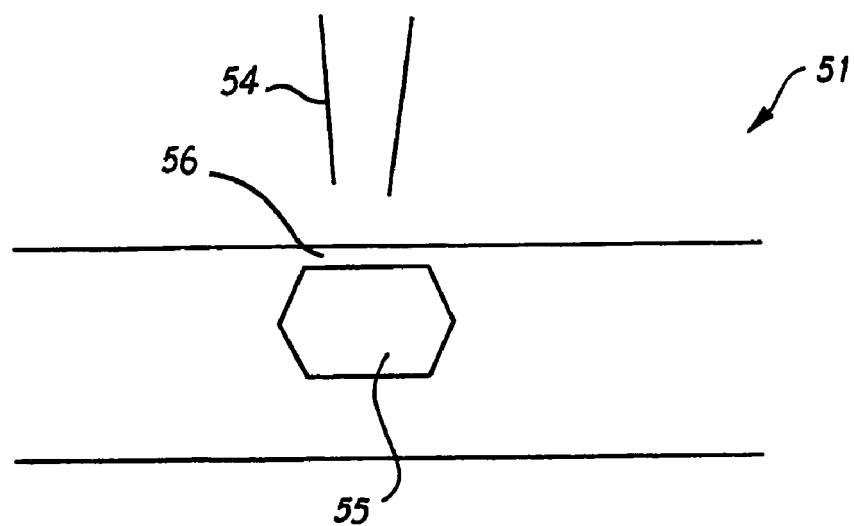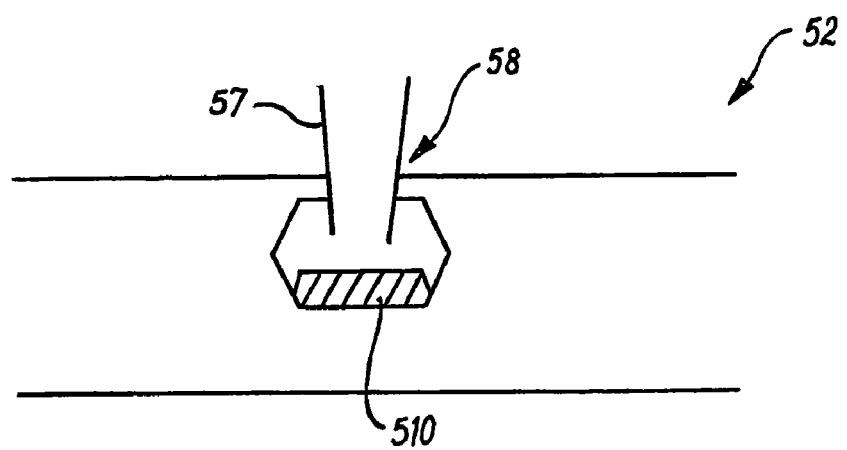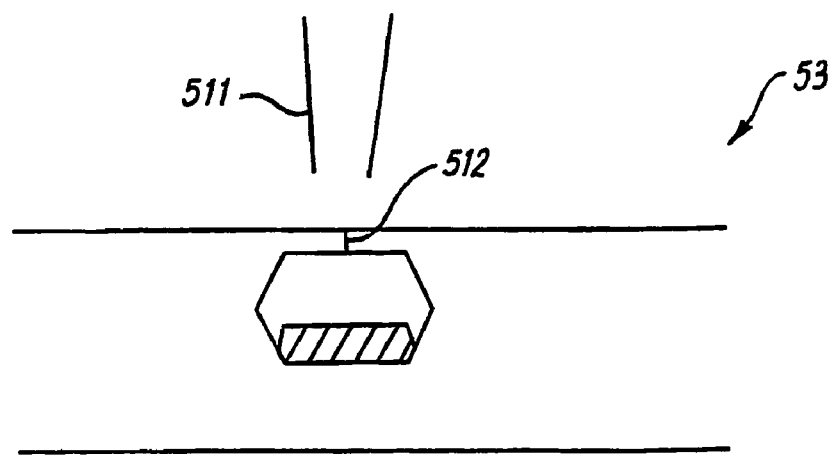
Fig. 5

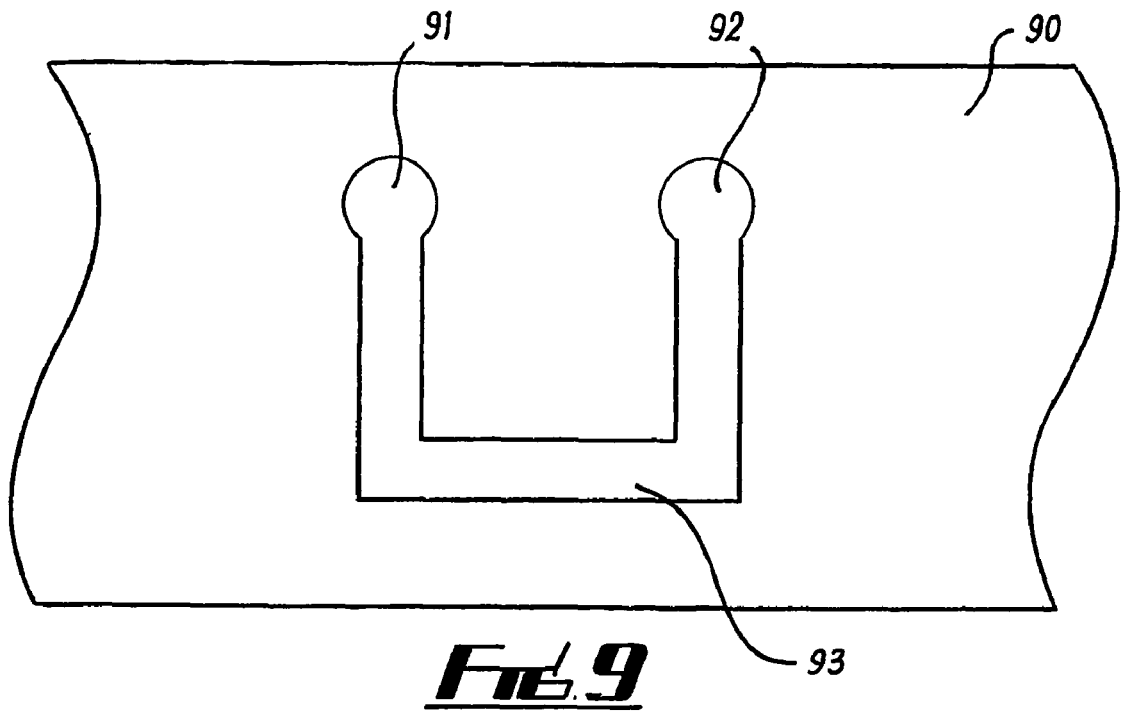
_FIG. 9_
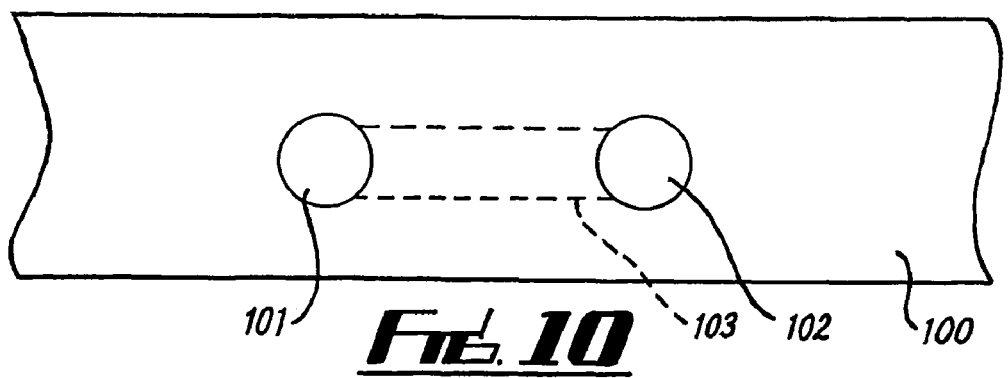
_FIG. 10_
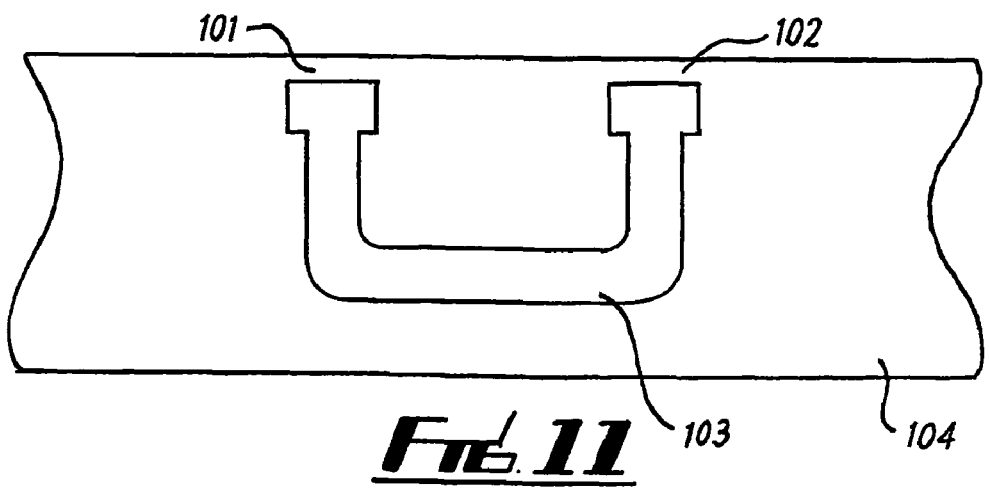
_FIG. 11_

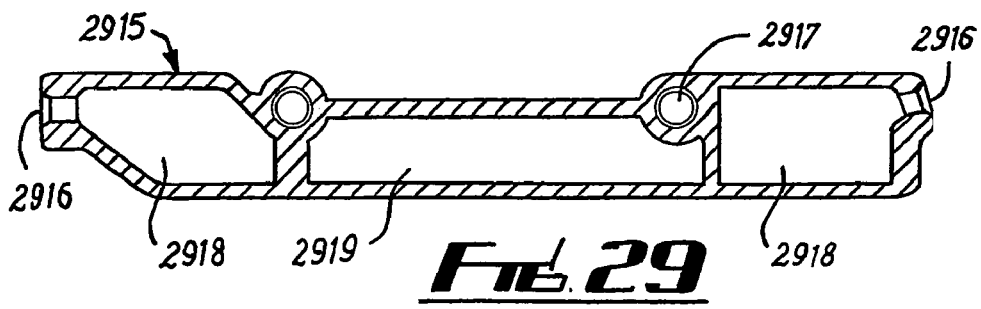
FIG. 29
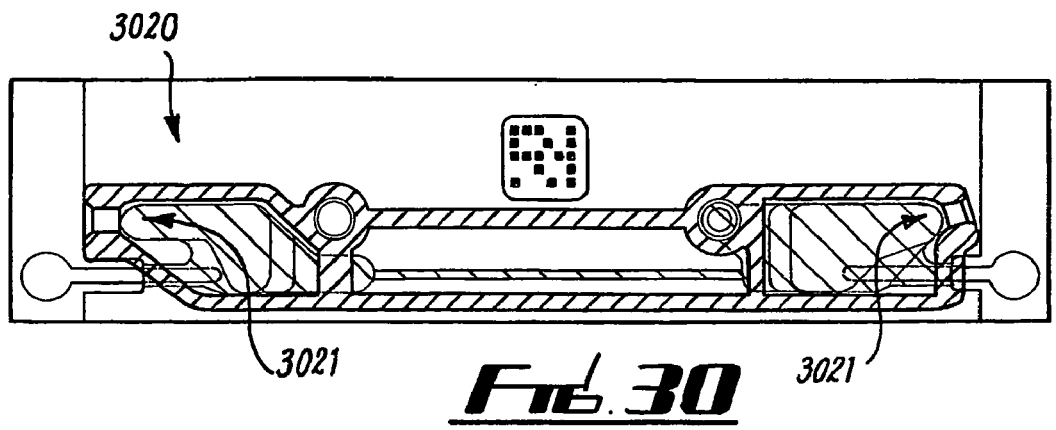
FIG. 30
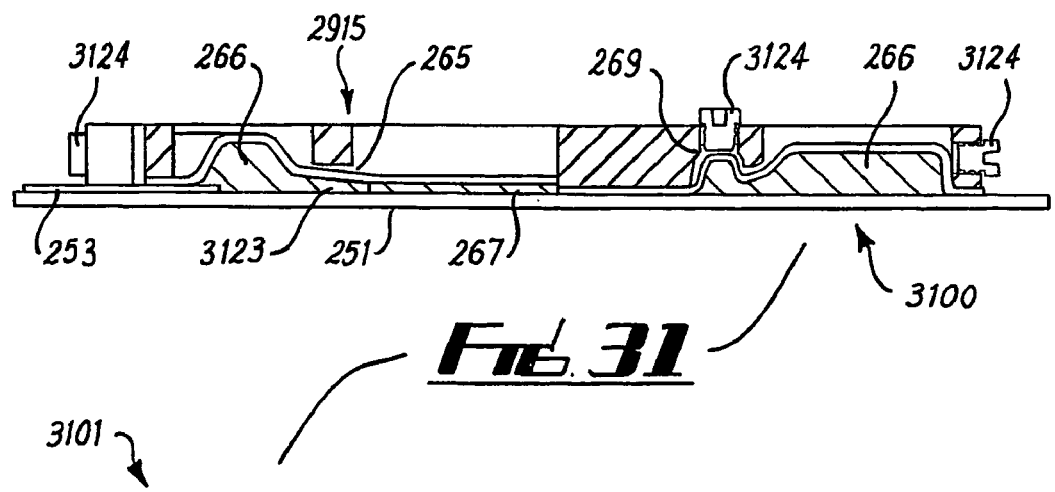
FIG. 31
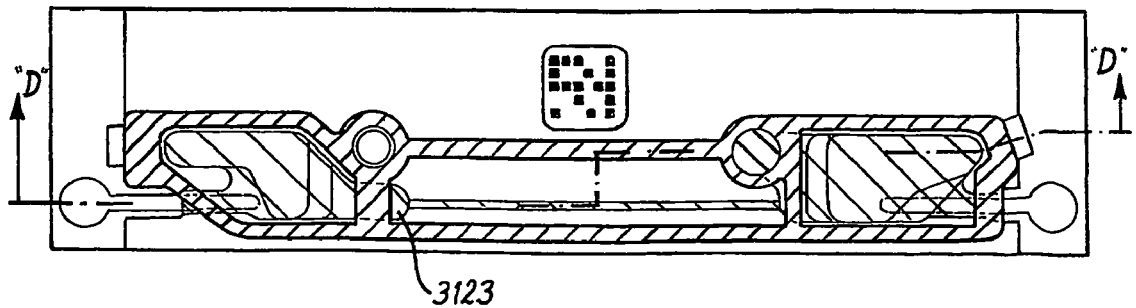

APPARATUS AND METHODS FOR MICROFLUIDIC APPLICATIONS

CROSS-REFERENCE TO RELATED APPLICATIONS

This application is the national phase of International (PCT) Patent Application Ser. No. PCT/GB02/05367, filed Nov. 27, 2002, published under PCT Article 21(2) in English, which claims priority to and the benefit of British Patent Application No. 0128350.6, filed Nov. 27, 2001, the disclosures of which are incorporated herein by reference.

This invention relates to fabrication and processing technology for microfluidic applications in chemical and biological processing and analysis, in particular fabrication and application of non-rigid apparatuses optionally in the form of a tape.

BACKGROUND

In the field known as "lab-on-a-chip", electronic, microfluidic and bio processes are combined at chip scale to bring dramatic productivity and cost benefits to fields as diverse as high throughput screening, bio-molecular assays and point of care diagnostics.

Fabrication technologies are known that have been developed in the microelectronics industry and then applied to biotechnology and biomedical industries. However, compared to electronic based devices, biotechnology devices are much more diverse in order to enable the manipulation of a large variety of bio materials, fluids and chemicals. Improvements in performance, throughput and cost have been achieved by reducing the size and volume in miniaturised biosystems.

These "Lab-on-a-chip" solutions have increased the amount of functionality per apparatus by miniaturisation. The problem with increased miniaturisation is the complexity of smaller scale processing and the large cost of equipment for microfabrication. Furthermore, conventional lithographic and etching processes adopted from the microelectronics industry require rigid apparatuses.

Glass apparatuses for microfluidic applications are known, such as the LabCHIP from Caliper Technologies Corp (Mountain View, Calif.), U.S. Pat. No. 6,274,089. The glass apparatus is attached to a plastic moulded cartridge which incorporates wells for loading test samples, reagents and gel.

Rigid plastic apparatuses are known, such as the LabCard from Aclara Biosciences Inc (Mountain View, Calif.), U.S. Pat. No. 6,103,199. A tooling process involving patterning and electroplating is used to create embossed microchannels on the card surface.

"Lab-on-a-CD" devices such as from Gamera and Gyros use centrifugal force of a rotating disk as the microfluidic pumping mechanism, e.g., Gamera Bioscience Corporation (Medford, Mass.), U.S. Pat. No. 6,063,589.

The above are all discrete devices which require further handling steps for continuous operation. They are also inefficient for single test operation.

Silicon apparatuses are known, such as the eNanogen chip, which is a microfluidic microarray device, where the microarray is selectively doped with biological or chemical probes which can be polarised electrically to attract or repel molecules from the sample material under test.

For example, U.S. Pat. No. 5,858,195 to Lockheed Martin Energy Research Corporation (Oak Ridge, Tenn.) describes a microchip laboratory system and method to provide fluid manipulations. The microchip is fabricated using standard photolithographic procedures and etching, incorporating an apparatus and rigid cover plate joined using die bonding. Capillary electrophoresis and electrochromatography are performed in channels formed in the apparatus. Analytes are loaded into a four-way intersection of channels by electrokinetically pumping the analyte through the intersection.

These approaches require time consuming additional steps of picking and placing discrete apparatuses which increases the overall processing cycle time in microfluidic applications.

"MicroTape™—A 384 Well Ultra High Throughput Screening System" Journal of the Association for Laboratory Automation, May 1999: Volume 4, Number 2, p. 31, Astle, T. W., teaches of a tape device designed for storage of liquid compounds in smaller volumes (typically 10 ul) than the industry standard 96 or 384 well micro-titer plate (MTP). Tape storage is in a pattern identical to a 384 well MTP. In effect, MicroTape™ is an alternative passive storage medium to the micro-titer plate.

The primary features of MicroTape™ are:
1) bulk compounds typically stored in 96 or 384 well micro-titer plates can be transferred into a smaller volume storage medium, i.e. the MicroTape™, and then stored within the medium for future use at low temperature. When this array of compounds is required for test, only one section of tape (i.e. a 384 well section) need be retrieved and defrosted, rather than the whole of the bulk compound medium.
2) the MicroTape™ incorporates a separate sealing membrane to protect the compound during storage. This membrane is capable of being de-sealed and re-sealed.
3) use of MicroTape™ for Polymerase Chain Reaction (PCR) processing. The concept takes a reel/roll of MicroTape™ and uses alternate immersion in hot and cold water tanks to perform thermal cycling for the PCR process.

The limitations of this approach are:
It's well capacity is 10 ul which is much larger scale than lab-on-a-chip.
It is not patterned microfluidic channels.
It is not analytical, i.e. does not incorporate gels or analytes through which molecular separation or purification can be accomplished.
It is not electrically active, i.e. incorporating electrical elements or interfacing with electrical elements i.e. it is simply a carrier.
The PCR processing is performed on the whole reel rather than on selectable areas or segments of the tape.

In the contemporary art of gel electrophoresis, including the emerging field of miniaturised systems, a common means of detection is to capture an image of these layers using electro-optical means. A convenient method is to use a 2 dimensional CCD (Charged Coupled Device) detector array (an area array) to capture the appearance of the permeation layer area in a single "snapshot" image. Another convenient method is to use a 1 dimensional CCD array (a line array) and move it relative to the permeation layer such that the full image is built up from many adjacent line images.

It would be advantageous to provide an apparatus for microfluidic applications that allowed an increased area for microfluidic processing, without requiring an increase in miniaturisation and the associated complexity of processing.

It would be further advantageous to provide an apparatus for microfluidic applications that facilitated loading and transport of analytes and reagents both during and after apparatus fabrication.

It would be further advantageous to provide an apparatus that allowed continuous processing of a moving apparatus.

It would be further advantageous to provide an apparatus that allowed a variable area on one apparatus, while using a fixed size of apparatus handling mechanism.

It would further be advantageous to integrate information storage and management systems within or on the apparatus for use with simple detection methods.

It is an object of at least one aspect of the present invention to provide an apparatus for microfluidic applications.

It is a further object of at least one aspect of the present invention to allow an increased area for microfluidic processing and novel dynamic processing steps both within and of the apparatus, while using simple fabrication processes and apparatus handling techniques.

In this document, a probe is defined as including mechanical probes, electrical probes and pipettes for fluidic manipulation.

In this document, indexing patterns are defined as including patterns for facilitation mechanical movement, detection of position, detection of movement, and display and recording of information.

SUMMARY

In this document, mass transport is defined as transport of mass relative to the apparatus.

According to a first aspect of the present invention, there is provided an apparatus for microfluidic processing applications, wherein said microfluidic processing is performed on a selected area of a plurality of areas each individually selectable on said apparatus, characterised in that the apparatus is non-rigid.

According to a second aspect of the present invention, there is provided an apparatus for mass transport microfluidic processing applications, characterised in that the apparatus is non-rigid.

According to a third aspect of the present invention, there is provided an apparatus for microfluidic processing applications, characterised in that the apparatus comprises at least one rigid member and at least one non-rigid member.

Preferably the apparatus comprises at least two non-rigid members.

Preferably said non-rigid member is a tape.

Preferably there are a plurality of rigid members each associated with one of a plurality of areas each individually selectable on said apparatus.

Preferably said rigid member comprises access ports.

According to a fourth aspect of the present invention, there is provided a method of fabrication of an apparatus for microfluidic processing applications, comprising the step of attaching at least one rigid member to at least one non-rigid member.

Preferably said method of fabrication further comprises the step of forming at least one non-rigid member.

Preferably said step of forming said at least one non-rigid member comprises the step of high pressure plastic film forming with said high pressure acting on said apparatus.

Alternatively said step of high pressure plastic film forming is arranged with the high pressure acting on a compliant membrane, which is part of a forming tool in contact with said apparatus.

Preferably said rigid member has a maximum dimension perpendicular to its plane greater than the maximum dimension perpendicular to the plane of said at least one non-rigid member.

According to a fifth aspect of the present invention, there is provided a method of mounting an apparatus for microfludic processing applications, comprising the step of attaching said apparatus to a non-rigid carrier that is, in the form of a tape.

Preferably said carrier has a maximum dimension perpendicular to its plane greater than the maximum dimension perpendicular to the plane of said apparatus.

Preferably said apparatus is attached to said non-rigid carrier by snap fitting into apertures in said carrier.

Alternatively said apparatus is attached to said non-rigid carrier by ultrasonic welding, heat sealing, adhesive, chemical or molecular bonding.

Preferably said apparatus is a tape.

Preferably said apparatus comprises a polymer film.

Preferably said apparatus comprises processing elements for microfluidic processing.

Typically said processing elements comprise indents of said apparatus.

Optionally said processing elements comprise cavities embedded within said apparatus.

Optionally said processing elements comprise processing materials in intimate contact with the surface of said apparatus.

Optionally said processing elements comprise processing materials embedded within said apparatus.

Optionally said processing elements comprise opaque, translucent or coloured materials for providing optical isolation between elements or providing indexing marks.

Preferably an element of said apparatus is transparent.

Preferably a member of said apparatus is transparent.

Preferably said apparatus is penetrable.

Preferably said apparatus is self sealing during penetration.

More preferably said apparatus is self sealing after penetration.

Preferably said apparatus further comprises an impermeable membrane.

Preferably said impermeable membrane is affixed in intimate contact with parts of the surface of said apparatus.

Alternatively said impermeable membrane is arranged as discrete areas of impermeable membrane in intimate contact with parts of the surface of said apparatus.

Preferably said impermeable membrane is penetrable.

Preferably said impermeable membrane is self sealing during penetration.

More preferably said impermeable membrane is self sealing after penetration.

Optionally said impermeable membrane is re-sealed by a capping element after penetration.

Preferably said impermeable membrane is supported by support structures.

Preferably said apparatus further comprises a non-rigid member.

Preferably said non-rigid member is affixed in intimate contact with parts of the surface of said apparatus.

Alternatively said non-rigid member is arranged as discrete areas of non-rigid member in intimate contact with parts of the surface of said apparatus.

Preferably said non-rigid member is penetrable.

Preferably said non-rigid member is self sealing during penetration.

More preferably said non-rigid member is self sealing after penetration.

Optionally said non-rigid member is re-sealed by a capping element after penetration.

Preferably said non-rigid member is supported by support structures.

According to a sixth aspect of the present invention, there is provided a method of fabrication of an apparatus for mass transport microfluidic processing applications comprising the step of forming an apparatus that is non-rigid.

According to a seventh aspect of the present invention, there is provided a method of fabrication of an apparatus for mass transport microfluidic processing applications comprising the step of fabricating a tape.

Preferably said step of forming said apparatus comprises the step of high pressure plastic film forming with said high pressure acting on said apparatus.

Alternatively said step of high pressure plastic film forming is arranged with the high pressure acting on a compliant membrane, which is part of the forming tool in contact with said apparatus.

Optionally said step of fabricating said apparatus further comprises the step of preloading processing materials onto said apparatus before fabrication.

Optionally said step of fabricating said apparatus further comprises the step of loading processing materials onto said apparatus during fabrication.

Typically said step of preloading or loading during fabrication of said apparatus comprises the step of depositing processing materials onto a carrier.

Typically said step of preloading or loading during fabrication of said apparatus comprises the step of depositing processing material onto a non-rigid member.

Preferably said deposited processing material comprises permeation layers.

Alternatively said deposited processing material comprises conductive material.

Alternatively said deposited processing material comprises chemically or biologically active material.

Alternatively said deposited processing material comprises marks for identity purposes.

Alternatively said deposited processing material comprises magnetisable material.

Preferably said step of depositing comprises printing.

Alternatively said step of preloading or loading during fabrication of said apparatus is performed by a preloading or loading process selected from a list of processes comprising: deposition and etching, injection into a cavity and injection into an indentation.

Preferably said method of fabrication of said apparatus further comprises the steps of depositing patterns on an apparatus and forming said apparatus, wherein the localised formation of said processing elements is responsive to the distortion by said forming of said deposited pattern.

Preferably said method of fabrication of said apparatus further comprises the steps of depositing patterns on an apparatus and localised formation of said apparatus is responsive to the topography of said deposited pattern, resulting in the formation of said processing elements.

Preferably said step of depositing comprises pre-printing.

According to an eighth aspect of the present invention, there is provided a method of fabrication of an apparatus for mass transport microfluidic processing applications, comprising the step of including an impermeable membrane as part of said apparatus.

Preferably said step of including an impermeable membrane comprises the step of affixing an impermeable membrane to a substrate.

Optionally, said step of including an impermeable membrane comprises the step of depositing, overlaying or affixing discrete areas of impermeable membrane in intimate contact with parts of the surface of said apparatus.

Optionally, said step of including an impermeable membrane comprises the step of depositing, overlaying or affixing an impermeable membrane on said apparatus and selectively removing areas of said impermeable membrane.

Optionally, said selected removal of said impermeable membrane is performed by the step of cropping.

According to a ninth aspect of the present invention, there is provided a method of fabrication of an apparatus for mass transport microfluidic processing applications, comprising the step of including a non-rigid member as part of said apparatus.

Preferably said step of including a non-rigid member comprises the step of affixing a non-rigid member to a substrate.

Optionally, said step of including a non-rigid member comprises the step of depositing, overlaying or affixing discrete areas of non-rigid member in intimate contact with parts of the surface of said apparatus.

Optionally, said step of including a non-rigid member comprises the step of depositing, overlaying or affixing a non-rigid member on said apparatus and selectively removing areas of said non-rigid member.

Optionally, said selected removal of said non-rigid member is performed by the step of cropping.

According to a tenth aspect of the present invention, there is provided a method of microfluidic processing, comprising the steps of selecting an area of a plurality of areas of an apparatus and performing microfluidic processing at said selected area, characterised in that said apparatus is non-rigid.

Optionally said step of performing microfluidic processing comprises contacting at least one conducting element that connects the exterior of said apparatus to the interior of said apparatus.

Preferably said method further comprises the step of providing an electrical potential to at least one conducting element.

Preferably said method further comprises the step of enabling an electrical current to pass through said least one conducting element.

Preferably said apparatus is a tape.

Preferably said microfluidic processing is mass transport microfluidic processing.

Preferably said microfluidic processing is responsive to the deformation of said apparatus.

Preferably said deformation comprises deformation by a step selected from a list of steps comprising: bending, flexing, folding, twisting, conforming to a rigid surface, mechanical deformation, deformation by applying a sound pressure, deformation by applying a liquid pressure, and deformation by applying a gas pressure.

Typically said gas pressure is a negative pressure.

Optionally said deformation may further comprise the step of bringing part of said apparatus back into contact with another part of itself.

Alternatively, said step of deformation further comprises the step of bringing a part of said apparatus into contact with another apparatus.

Optionally said deformation of said apparatus comprises the step of moving part of said apparatus into a position for processing of said part of said apparatus.

Typically said position for processing is a position with said apparatus in contact with a processing tool.

Preferably said microfluidic processing is responsive to said deformation of said apparatus, said microfluidic processing being selected from a list comprising pumping, filling, pouring, pressurising, mixing, dispensing, aspirating, separating, combining, heating and cooling.

According to an eleventh aspect of the present invention, there is provided a method of processing for microfludic processing applications, characterised in that the processing comprises the step of piercing an impermeable membrane.

Preferably said step of piercing an impermeable membrane is performed with at least one probe.

Optionally said at least one probe comprises at least one pipette.

More preferably said method of processing further comprises the step of providing an electrical potential to at least one conducting probe that has pierced said membrane.

Alternatively said step of processing further comprises the step of enabling an electrical current to pass through at least one conducting probe that has pierced said membrane.

According to a twelfth aspect of the present invention, there is provided a method of processing for microfludic processing applications, characterised in that the processing comprises the step of piercing an apparatus.

Preferably said apparatus is self sealing during said step of piercing.

Preferably said apparatus is self sealing after said step of piercing.

Optionally said apparatus is re-sealed by a capping element after penetration.

Preferably said step of piercing the apparatus is performed with at least one probe.

Optionally said at least one probe comprises at least one pipette.

More preferably said method of processing further comprises the step of providing an electrical potential to at least one conducting probe that has pierced said apparatus.

Alternatively said step of processing further comprises the step of enabling an electrical current to pass through a conducting probe that has pierced said apparatus.

According to a thirteenth aspect of the present invention, there is provided an apparatus for microfluidic processing applications, characterised in that the apparatus is a non-rigid tape comprising a plurality of indexing patterns.

Preferably said indexing patterns are rigid members.

Preferably said indexing patterns are repeated.

Preferably said indexing patterns are arranged to facilitate detection of position.

Typically said indexing patterns are arranged to facilitate detection of position using optical detection.

According to a fourteenth aspect of the present invention, there is provided a method of transporting a tape apparatus for microfluidic applications comprising the step of moving said apparatus by interaction of a moving object with at least one rigid member attached to said apparatus.

BRIEF DESCRIPTION OF THE DRAWINGS

In order to provide a better understanding of the present invention, an embodiment will now be described by way of example only and with reference to the accompanying figures in which:

FIG. 3 illustrates processing elements incorporating impermeable membranes comprising homogeneous apparatus material;

FIG. 5 illustrates the insertion and removal of a probe into a processing element through an impermeable self-sealing membrane;

FIG. 9 illustrates in schematic form a plan view of a structure for probing through an impermeable membrane;

FIG. 10 illustrates an alternative arrangement to that of FIG. 9 where the channel extends into the apparatus;

FIG. 11 illustrates a cross-section of the structure illustrated in FIG. 10;

FIG. 29 illustrates in schematic form an exoskeleton;

FIG. 30 illustrates in schematic form an exoskeleton affixed to the supporting/patterned layer;

FIG. 31 illustrates in schematic form a section (vertical scale exaggerated for clarity) and plan view through one tape segment and disposition of sealing plugs;

DETAILED DESCRIPTION

The invention is a non-rigid apparatus for microfluidic processing applications, which may be in the form of a tape.

The use of a non-rigid apparatus allows novel dynamic processing methods. The incorporation of re-sealable impermeable layers allows further novel dynamic processing steps.

Figure 1A:
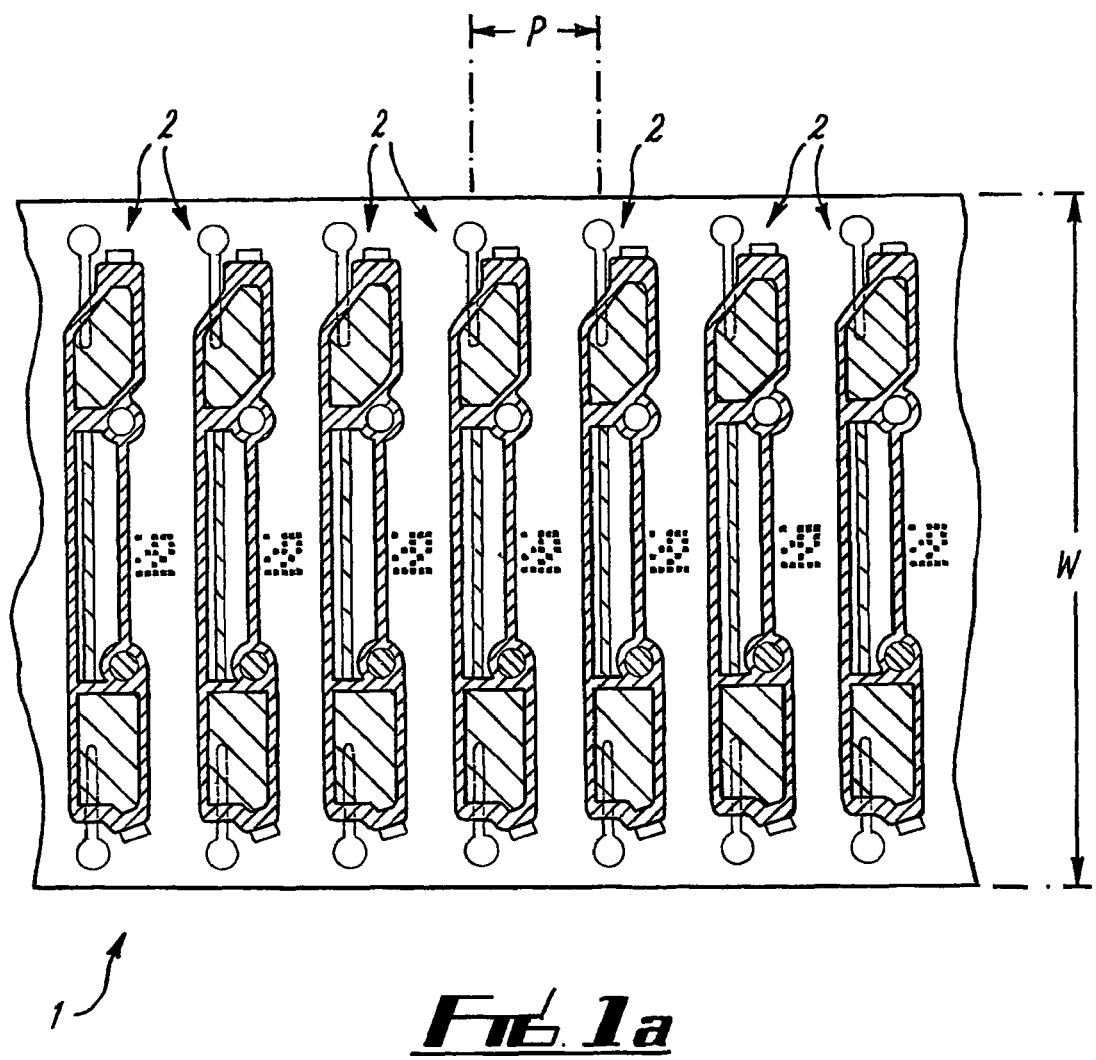
FIG. 1 illustrates in schematic form non-rigid apparatuses, showing a section of tape and an enlargement of one area suitable for gel electrophoresis in accordance with the present invention.

FIG. 1a shows a typical section of tape 1 with an array of microfluidic processing areas or processing segments 2 in accordance with a preferred embodiment of the present invention. Adjacent test segments are spaced to suit the sample supply vessel. For example, where samples are delivered for test in a 384 well microtiter plate format, the tape segments will be supplied on a 4.5 mm pitch, P. The tape is processed in a vertical plane with the sample loading ports uppermost. The tape width, W, is typically 25 mm but is configurable in a range of 1 mm to 100 mm.

Figure 1B:
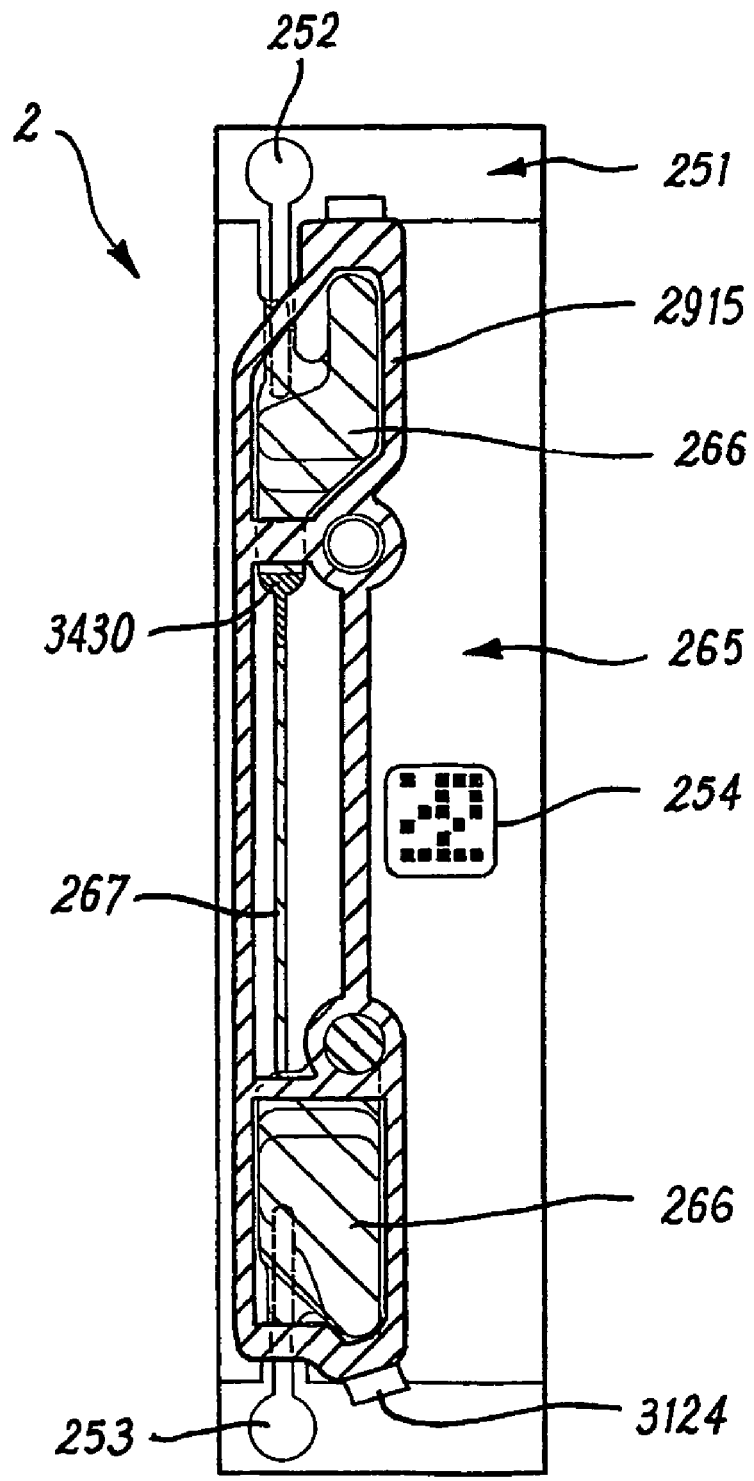

FIG. 1b shows an enlargement of a single processing segment 2, the operation of which follows well-established principles of electrophoresis. A DNA test sample is assumed.

The apparatus includes a supporting layer 251, a formed pattern layer 265 with a machine readable index mark 254. The pattern layer has formed cavities 266 and a connecting channel 267 filled with gel. The exoskeleton 2915 supports plugs 3124 that are used for re-sealable access to the cavities.

A DC voltage in the range 5 to 500 Volts (typically 100V/cm has been found to be suitable) will be applied across negative terminal 252 and positive terminal 253. This will cause the negatively charged DNA sample 3430 to migrate into the gel column 267 and its constituent molecules will then separate into bands in accordance with their molecular weight. An image of the band pattern will be captured by a commercial CCD camera and the image processed and presented to the user on a computer screen.

The electrical terminal pads 252 and 253 are conveniently presented for perpendicular access by external contact pins whose engagement will be controlled by the tape processing instrument. The exoskeleton 2915 may be conveniently employed as the tape transport means, and be driven by, for example, a toothed belt or a drive pinion having the same tooth pitch as the test segments on the tape.

The CCD image capture system can also conveniently capture the test segment ID mark, thus avoiding the need for a separate device such as a bar code reader.

Figure 2A:
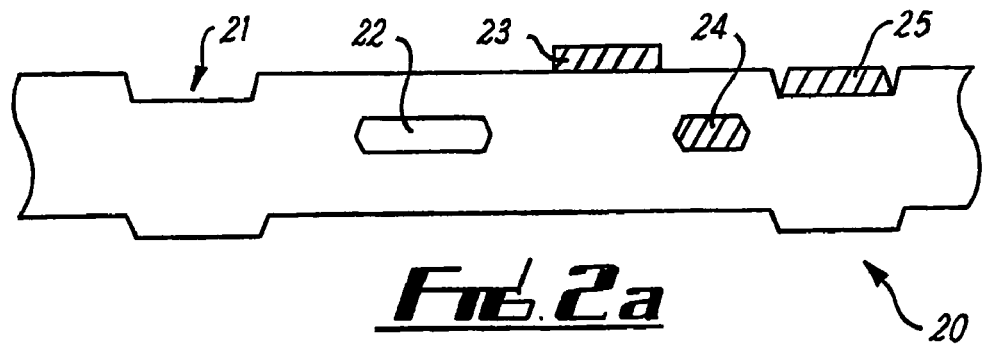
FIG. 2 illustrates in schematic form a variety of processing elements in accordance with the invention.

FIG. 2a illustrates a part of an apparatus 20 in cross-section. The apparatus contains a variety of processing elements which are an indent 21, a void or cavity in the apparatus 22 processing materials on the surface of the apparatus 23, processing materials embedded within the apparatus 24, and processing materials in an indent on the surface of the apparatus 25.

Figure 2B:
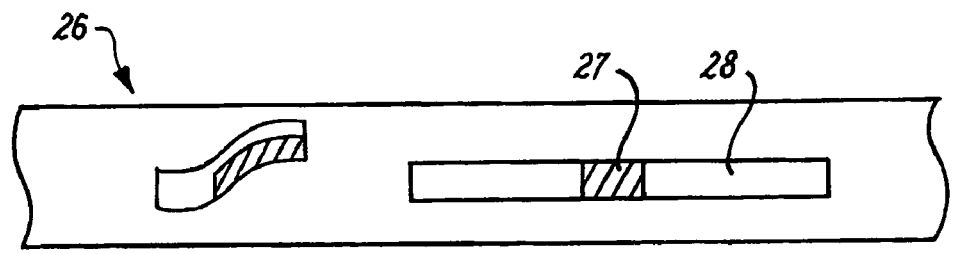

FIG. 2b illustrates part of an apparatus in cross-section with processing materials partially filling the height of a cavity in the apparatus 26 and processing material 27 embedded in a channel 28 within the apparatus.

The processing elements may comprise geometries which have sloping, curved or stepped surfaces. The processing materials may be conformal layers in intimate contact with surfaces of the apparatus. The processing elements may be opaque, translucent or coloured in order to provide optical isolation between elements or, alternatively, to provide indexing marks for allowing detection of movement and position of the apparatus.

Several of the processing elements shown in FIGS. 2a and 2b may be linked together, for example by cavities or indented troughs, which are themselves processing elements such that the linked elements act as a single processing group.

Figure 2C:
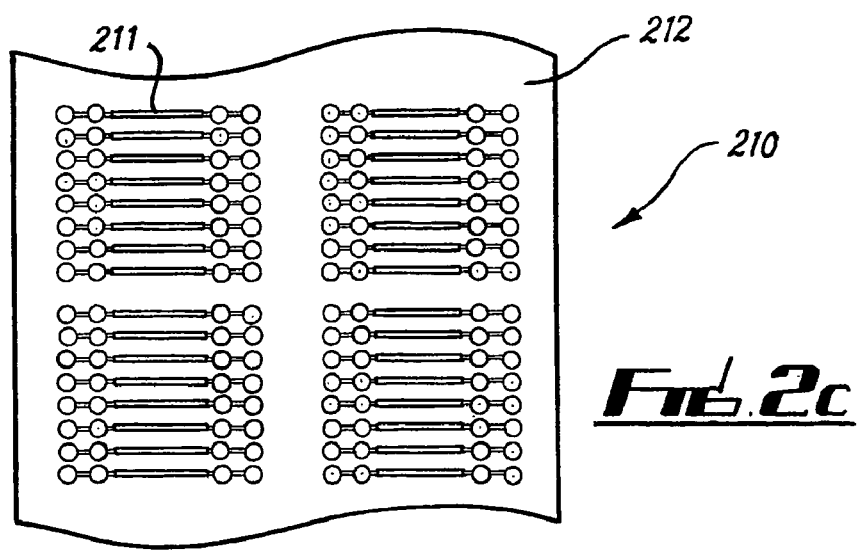
Figure 2D:
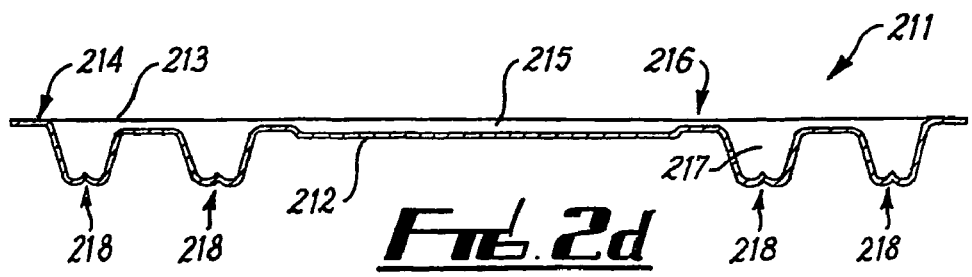

FIG. 2c illustrates a plan view 210 of processing element groups 211 on part of an apparatus 212. FIG. 2d illustrates a cross section of one of the processing element groups 211 shown in FIG. 2c. The formed plastic substrate 212 has a plastic membrane film 213 attached 214. The membrane is typically 0.1 mm thick, but could be as thin as 0.02 mm. An indented trough 215 is provided for processing materials such as materials based on Agarose or polyacrylamide gel. A channel 216 is provided for a plug that can be removed by, for example, laser ablation in order to allow processing material transport between the indented trough 215 and another processing element, indent 217. The substrate indents have pips 218 that are shaped to guide a probe such as a pipette to an area of the lower surface for penetration into the processing elements, for example indent 217. The substrate may be self-sealing during and after such penetration.

The processing materials can be gases, liquids, solids or semi-solids, e.g. biomolecular samples, fragments of DNA, biochemical polymers, chemical polymers, biomolecular modifiers, catalysts, antibodies, polypeptide molecules, protein molecules, biological organisms such as cells and viruses and permeation layers. The permeation layers may be solid, semi-solid, liquid, viscous, gelatinous or gaseous layers. The permeation layers may be biomolecular gates which are activated by electrical probes. The function of the biomolecular gates is defined by their particular depth, shape, volume and composition.

FIG. 3 shows a cross-section 30 of an apparatus for microfluidic processing applications. The apparatus contains a processing element 31 that is a cavity in the apparatus material. At the top of the cavity the apparatus material is thin, such that there is a membrane 32 that is impermeable and acts as an hermetic seal to protect the contents of the cavity.

The apparatus contains another processing element 33, where the membrane is configured as a flap 34, such that the cavity is sealed when the unattached end of the membrane is in contact with the apparatus 35.

FIG. 3 illustrates another processing element 36 with a membrane arranged as a flap 37 and distortion of the apparatus 38 resulting in the opening of the flap at its unattached end 39.

FIG. 4a illustrates an apparatus 40 that includes the same type of processing elements as shown in FIG. 3, but in this case the impermeable membrane is deposited, overlaid or affixed as discrete areas of impermeable membrane in intimate contact with parts of the surface of the apparatus. In the first processing element 41, the impermeable membrane 42 provides a hermetic seal to the cavity 43.

Another processing element 44 shows the impermeable membrane 45 in intimate contact and attached to the apparatus at the left hand side 46 and configured as a flap in a sealing contact with the right hand side 47 of an indent in the apparatus 48. This flap may be opened by deforming the apparatus in the same way as described as above with reference to processing element 36.

In another processing element 49, the impermeable membrane 410 is deposited as a plug in an indent resulting in a cavity 411, the membrane again providing an hermetic seal.

Alternatively, the impermeable membrane is continuous with the tape (i.e. not discrete). This continuous configuration can also embody local flaps in the membrane and still be one continuous membrane.

Figure 4B:
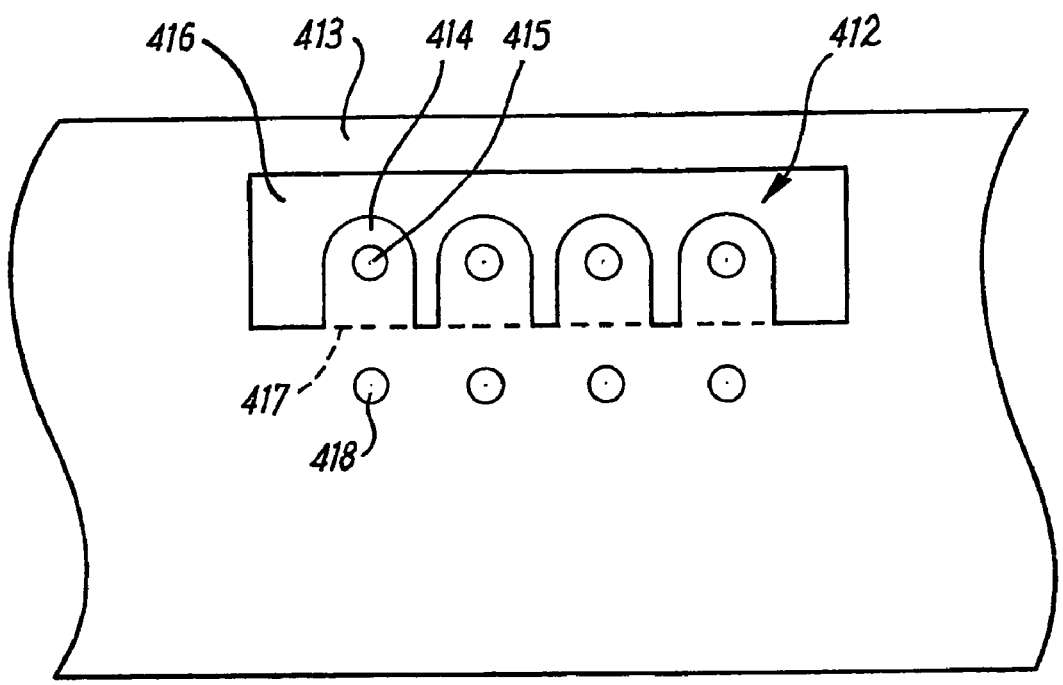
FIG. 4 illustrates impermeable processing elements incorporating discrete impermeable membranes and processing elements on hinged tabs.
Figure 4C:
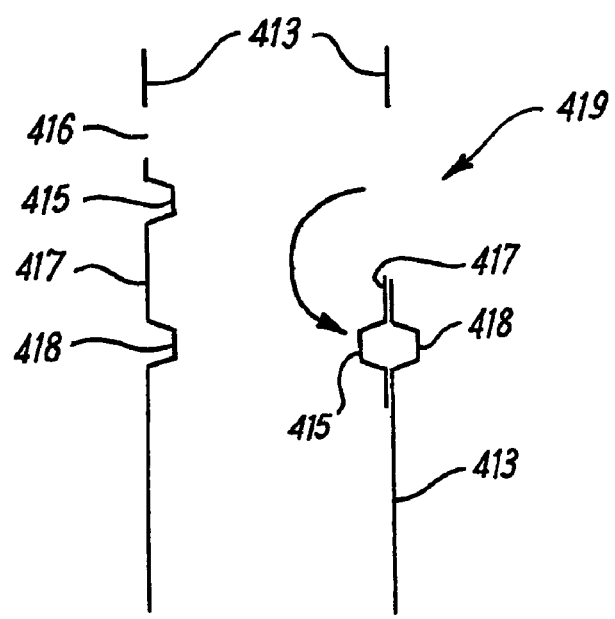

FIG. 4b illustrates a plan view and FIG. 4c illustrates cross-section views of a strip of apparatus 413 where a section of the apparatus had been removed 412 by punching out. The shape punched out has left several tabs 414 each with an indent 415 for containing processing materials. The tab 414 may be mechanically folded along the fold line 417. The fold line may be weakened by perforation or indenting. A second indent for processing materials 418 is positioned on the opposite side of the fold line from the indent 415. When the tab is folded over 419, the indent 415 is tipped over into contact with the indent 418, allowing mixing, pouring or transfer of processing materials between the two indents. This pouring may be assisted by the force of gravity, capillary action or external pressure. Alternative arrangements can be made that tilt through an angle of e.g. 30 degrees to cause pouring.

FIG. 5 shows a cavity during a sequence of steps before penetration 51, during penetration 52 and after penetration 53. The probe 54, which is a pipette, is to be inserted into the cavity 55 through the membrane 56. When the probe 57 is inserted through the membrane 58, the membrane is self-sealing, such that there is a seal between the probe and the membrane 58. Processing materials 510 are then deposited in the cavity. After removal of the probe 511, the impermeable membrane is self-sealing and a seal 512 is formed at the exit point of the probe. The penetration of the impermeable membrane can allow introduction of processing materials into cavities in the apparatus or removal of processing materials from the apparatus, the penetration of the membrane can allow the introduction of measurement tools into the apparatus or processing tools into the apparatus. When penetration is by a conducting probe, voltages can be applied that cause movement of fluids through processing materials using an electrokinetic method.

Figure 6:
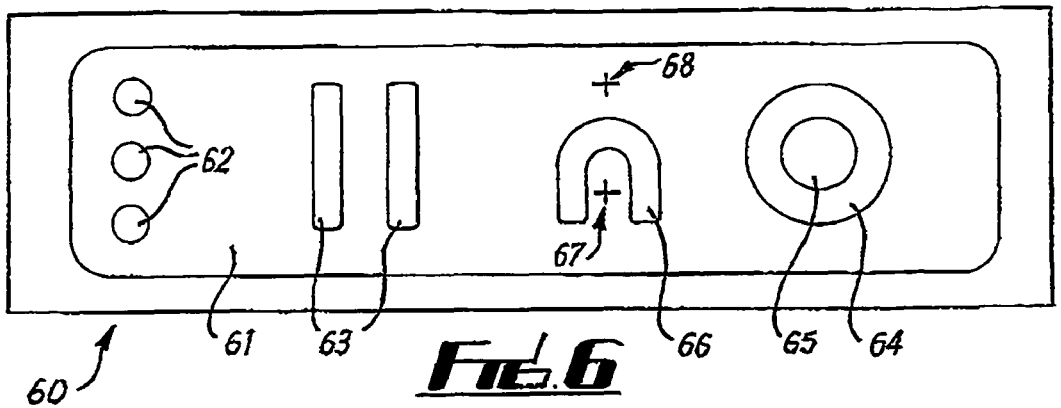
FIG. 6 illustrates a plan view of an apparatus incorporating an extended impermeable membrane with a variety of support structures.
Figure 7A:
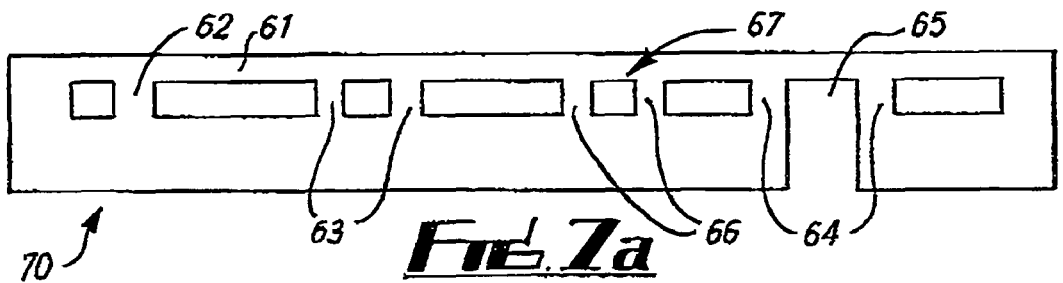
FIG. 7 illustrates a cross-section of the same structures illustrated in FIG. 6.
Figure 7B:
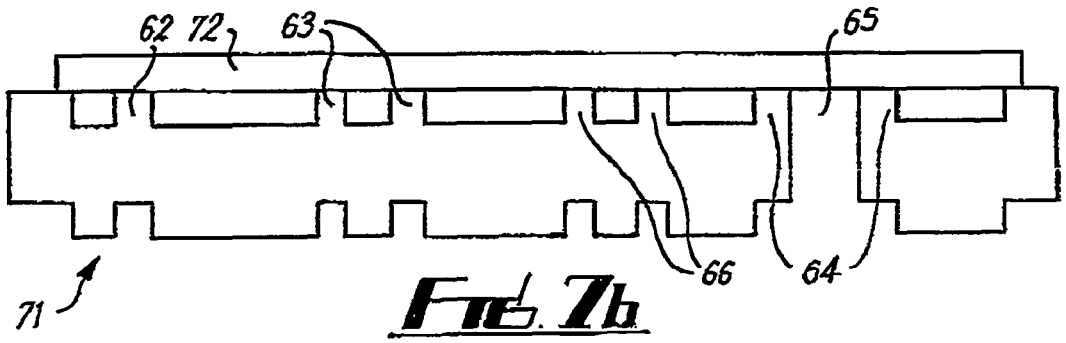

Large areas of membrane would tend to bend on attempted insertion of a probe. FIG. 6 shows a plan view of an apparatus 60 with an extended membrane 61 and support structures that provide support for the membrane adjacent to the location where probes are to penetrate the membrane. FIG. 7a shows a cross-section 70 of the same structure that is shown in the plan view of FIG. 6. FIG. 7b shows a cross-section 71 of the same structure that is shown in the plan view of FIG. 6, but with a continuous membrane 72 affixed to a substrate.

FIGS. 6 and 7 include support structures that are pillars 62, ribs 63 and an annulus 64. The centre of the annulus contains a membrane that may be penetrated by a probe. The annulus allows a "via" hole 65 to be created all the way through the apparatus and through which a wire or conducting probe can be passed so that a magnetic field can be created to interact with the adjacent processing area of the apparatus.

Another useful structure is a circular indent but still connected to adjacent processing elements and an externally configured loop or coil of wire (or other conducting element) around that circular indent. The electrical/magnetic field created can be used to attract or trap or process the liquid in the circular indent.

A "U" shaped pillar 66 is shown and a probe that enters in the centre of the "U" at point 67, marked with a plus, may be connected to a probe penetrating the impermeable membrane at the second penetration point 68 by an electrical, liquid or permeation path that is greater in length than the direct distance between the two penetration points.

Figure 8A:
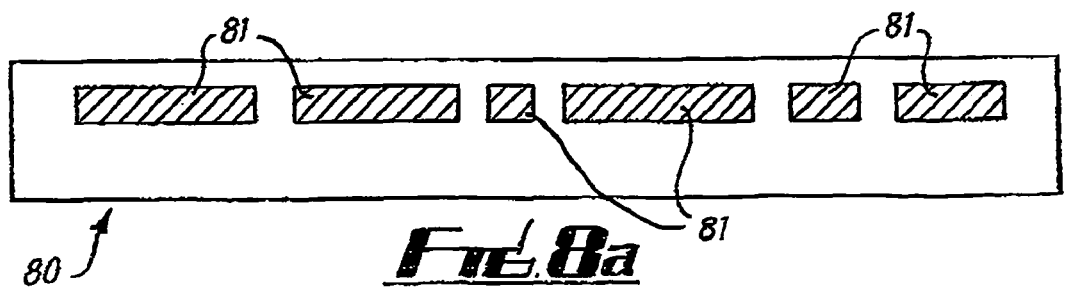
FIG. 8 illustrates some of the same structures in cross-section as FIG. 7, but where the processing elements comprise processing materials.
Figure 8B:
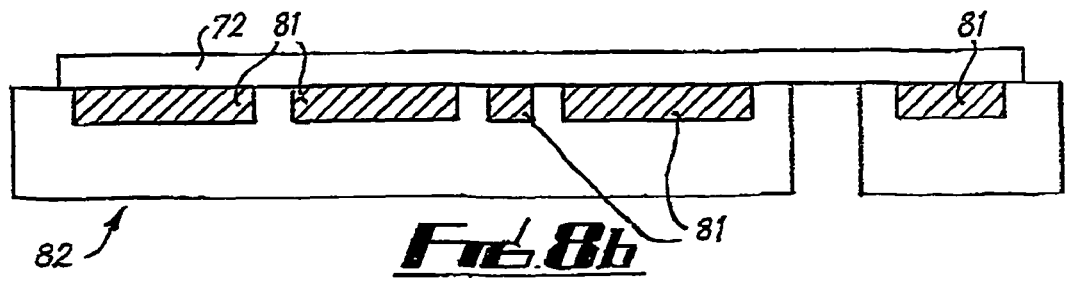

FIG. 8 shows a cross-section 80 of similar structures to those in FIG. 7, except that the cavities in the apparatus are filled with processing materials 81.

FIG. 9 shows a plan view of an apparatus 90 with a membrane that extends from a first penetration point 91 to a second penetration point 92 via an indented trough 93. A probe inserted through the impermeable membrane at the first penetration point 91 may be connected to a probe penetrating the impermeable membrane at the second penetration point 92 by an electrical, liquid or permeation path that is greater in length than the direct distance between the two penetration points.

FIG. 10 shows a plan view of an apparatus 100 with two membranes, each of which are penetration points 101 and 102. The dotted lines represent the edges of a buried channel 103 in between the two membranes.

FIG. 11 shows a cross-section through the line connecting the two penetration points of FIG. 10 which can be seen to be two membranes 101 and 102. The channel 103 extends into the depth of the apparatus 104. In this alternative arrangement the electrical, liquid or permeation path between tips of probes that are inserted through the penetration points are also greater than the direct distance between the two probes.

Turning FIGS. 10 and 11 through 90 degrees, illustrates side entry (rather than top entry) to the apparatus. Then FIG. 10 becomes a side view of the tape and FIG. 11 is a plan view of the plane of a strip of tape.

Figure 12:
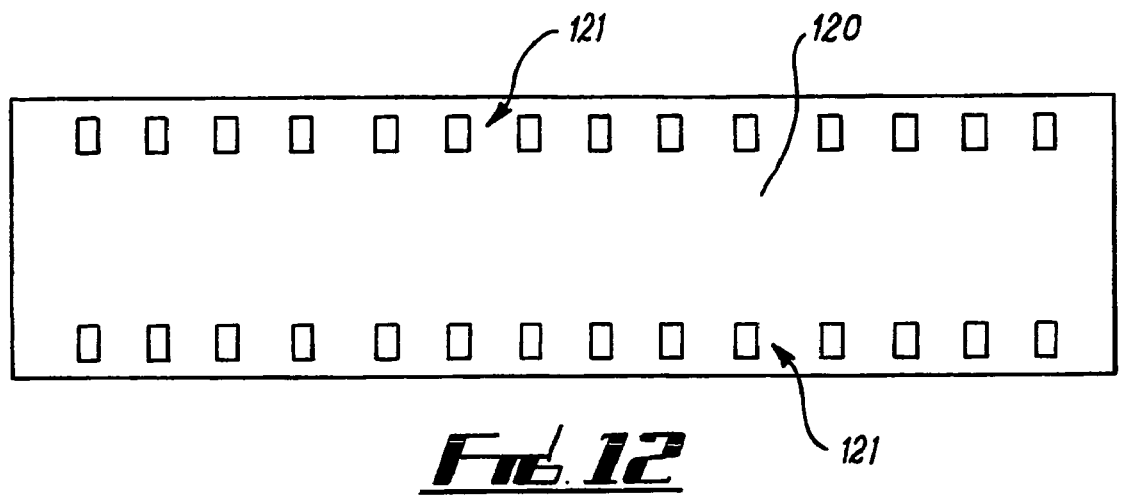
FIG. 12 illustrates a tape apparatus with indexing patterns.

With reference to FIG. 12, an apparatus 120 is shown in plan view with a plurality of indexing patterns 121. The indexing patterns may be opaque, translucent or coloured materials. The indexing patterns may be surface patterns, such as indents or process materials or raised patterns of apparatus material, for example the exoskeleton (2915 in FIG. 1b and 29). Alternatively, the indexing patterns may be embedded within the apparatus or patterns of magnetism in a magnetic film or perforations through the depth of the apparatus. Indexing patterns are arranged to facilitate traction of the apparatus and detection of position using optical, electromagnetic, electrochemical, electrical or other forms of detection. The indexing patterns may also record information related to the apparatus processing elements or the apparatus processing materials on the apparatus or within it processing results, processing status, processing time, processing location or processing identity. An indexing pattern may be a strip of material which functions as a data recording medium, for example magnetic or magneto-optical tape. Such tape may be written to and read by standard methods.

Figure 13:
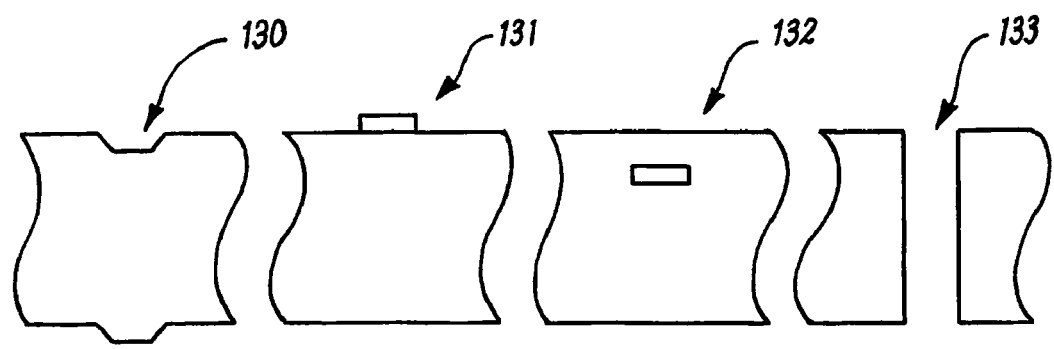
FIG. 13 illustrates in schematic form a variety of cross-sections of indexing patterns.

With reference to FIG. 13 that shows in schematic form a variety of cross-sections of indexing patterns, an indexing pattern is shown as an indent 130, a raised feature 131, an embedded feature 132 or a hole 133 punched through the apparatus.

Figure 14A:
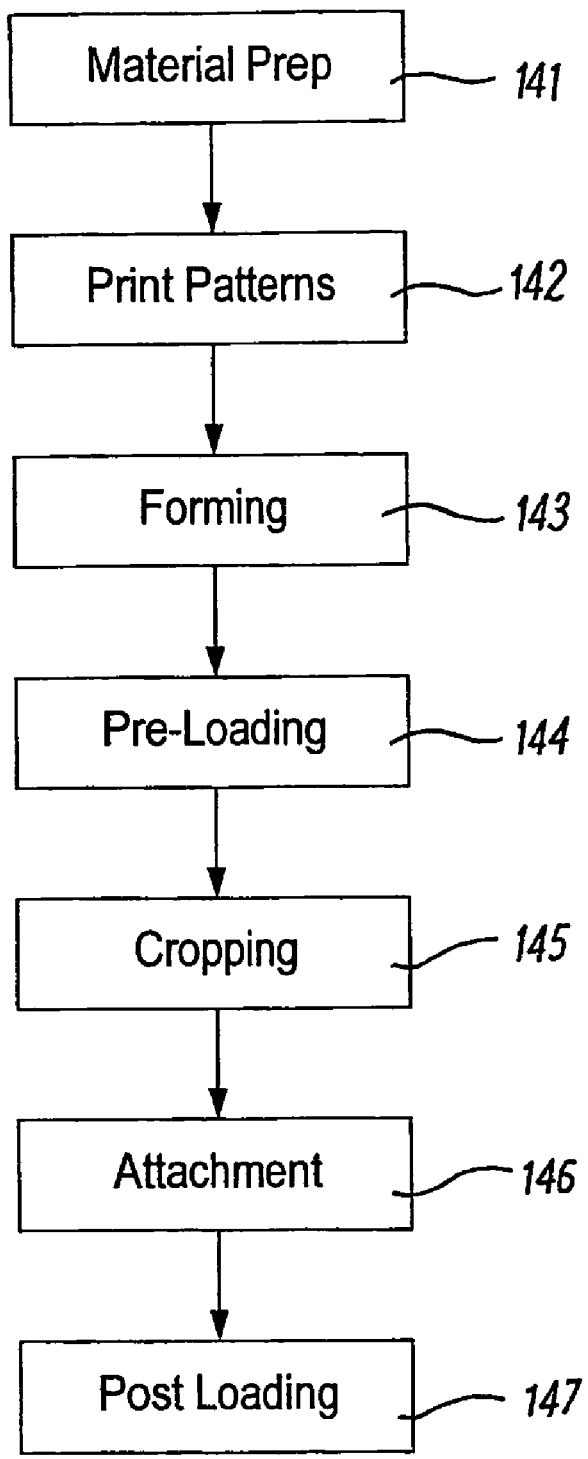
FIG. 14 illustrates a flow chart describing the steps of fabrication of an apparatus.

With reference to FIG. 14a, a flow chart is shown which describes the general process steps for the fabrication of non-rigid apparatuses for microfluidic processing applications, including apparatuses in the form of a tape or apparatuses of homogeneous material which may be assembled to a tape or discrete microfluidic devices which may be assembled to a tape.

Firstly, raw material preparation is provided, 141, the primary material will be a flexible substrate, preferably in the form of a continuous tape but other substrates, membranes, films, mouldings, skeletal structures or pre-assembled microfluidic devices may be part of the fabrication "kit".

Patterns can be pre-printed 142, preferably on a flat plastic non-rigid substrate. These patterns may be conductive elements, chemically or biologically active zones, magnetisable zones, or printed marks for identity purposes.

The apparatus, 143, is formed using high pressure thermoforming with the high pressure acting on the apparatus or the high pressure acting on a compliant membrane which is part of the forming tool that is in contact with the apparatus. The high pressure may be delivered by a gas or a fluid. During forming, the pre-printed patterns on the tape surface may be distorted in response to the topography of the formed processing elements. The final position of the pre-printed pattern material may be predicted by calibration test runs or simulation in order to design pre-printed patterns that distort to create processing elements that comprise the processing material that has been pre-printed. Alternatively, the forming of an apparatus may be performed by stereolithography or selective laser sintering. While forming the apparatus by stereolithography or selective laser sintering, processing elements may be included in the apparatus either by direct patterning or in response to the topography of the pre-printed patterns on the carrier.

The fabrication of the apparatus can further comprise the step of preloading processing materials 144. These processing materials may be preloaded by processes such as printing, film deposition and etching, stereo-lithography, injecting into a cavity and also injection into an indentation. Alternatively, the preloading may be achieved by tilting the apparatus with respect to gravity in order to open flaps of impermeable membrane so as to introduce processing materials through the open flaps into underlying structures. Alternatively these flaps may be opened by the distortion of the apparatus, such as conforming it to a rigid roller or corner.

A cropping operation 145 can be incorporated (optionally before the preloading step) to insert apertures in a substrate or finish a substrate to a defined external profile.

Apparatus assembly can continue, 146, by attachment or assembly of other layers, for example, a sealing layer or sealing layers, or sealing plugs, or additional supporting layers to improve the robustness of the apparatus, or other pre-assembled devices. The attachment methods may include a mechanical snap-fit, a mechanical interference fit, ultrasonic welding, heat sealing, molecular, chemical or adhesive bonding. Typically the final layer of apparatus that is affixed results in one or more impermeable membranes as part of the apparatus. Alternatively, the membranes may be formed by depositing, overlaying or affixing discrete areas of impermeable membrane in intimate contact with parts of the surface of the apparatus. Alternatively the formation of the impermeable membrane may be performed by depositing a film of impermeable membrane across the apparatus and selectively removing areas of the impermeable membrane. This selective removal may be performed using cropping/blanking or by lithography, such as photolithography, for patterning combined with wet or dry etching. These membranes are optionally formed of homogeneous apparatus material in the case of formation using stereo-lithography or selective laser sintering.

The apparatus can incorporate a further loading sequence, 147, of chemical or biological agents such as solvents, electrolytes, gels, stainers, dyes, affinity tags or bio-sensors. This loading may be achieved by pipette probe through the apparatus membrane or through an access port or access ports in the apparatus.

Figure 14B:
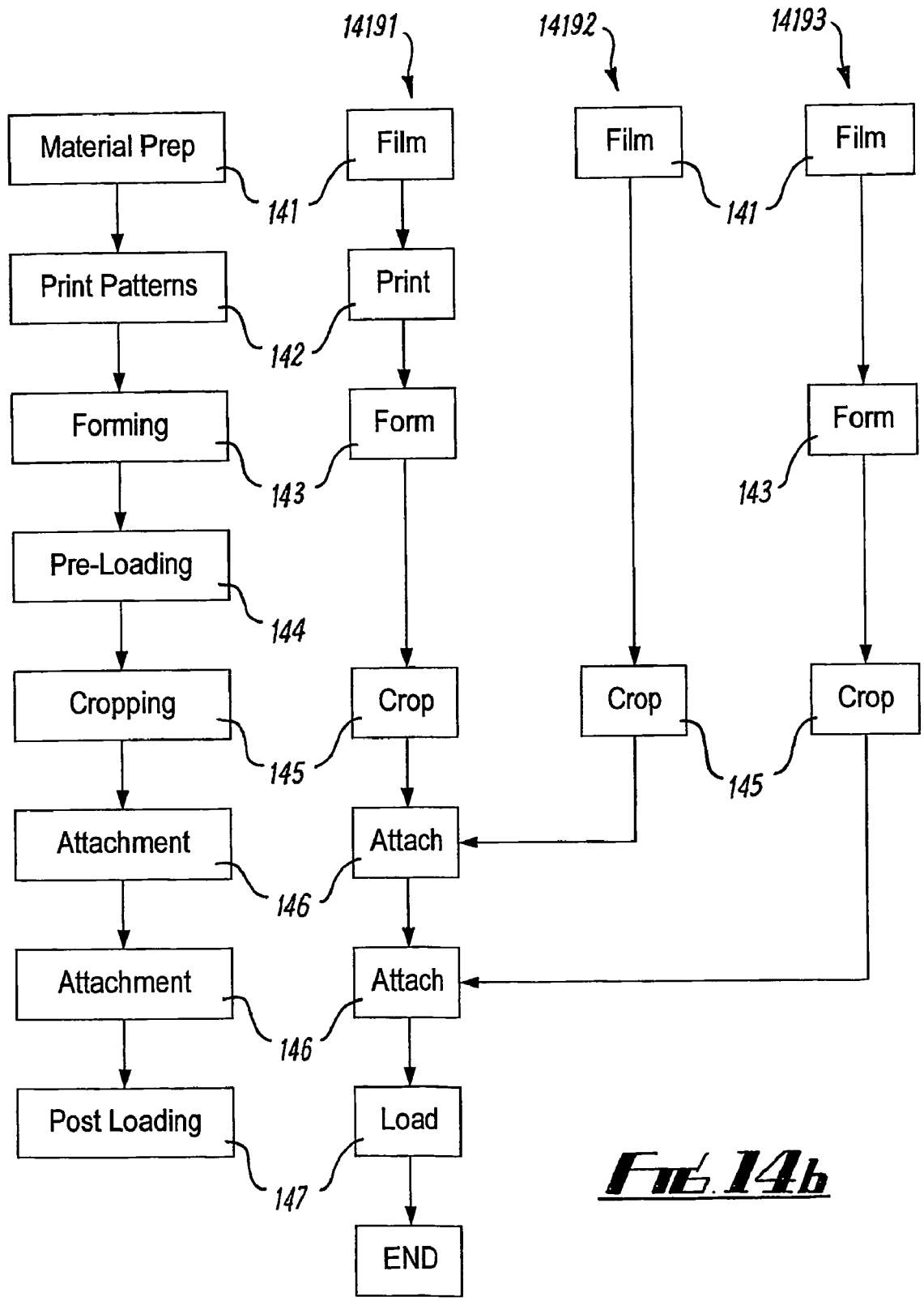
Figure 14C:
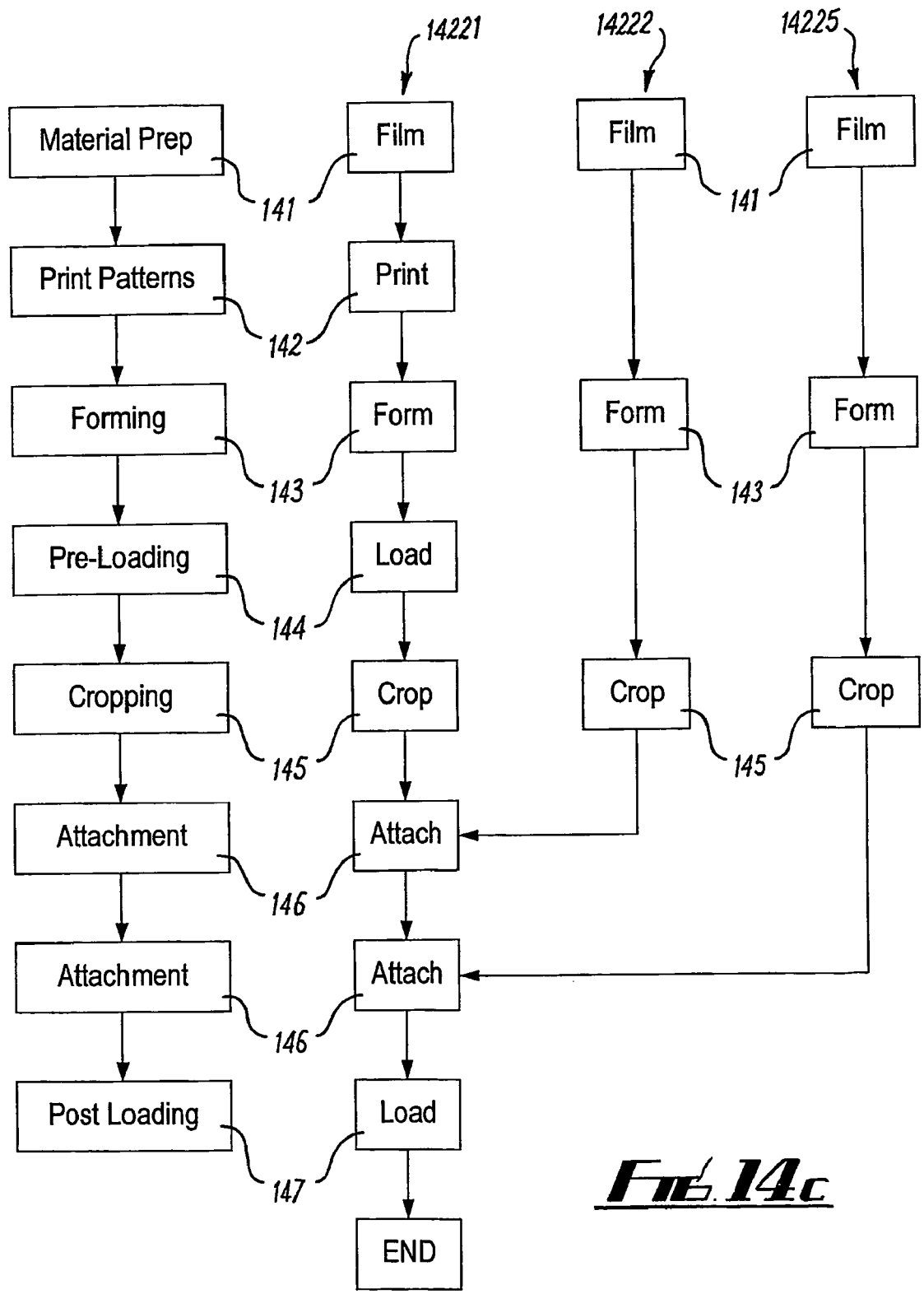
Figure 14D:
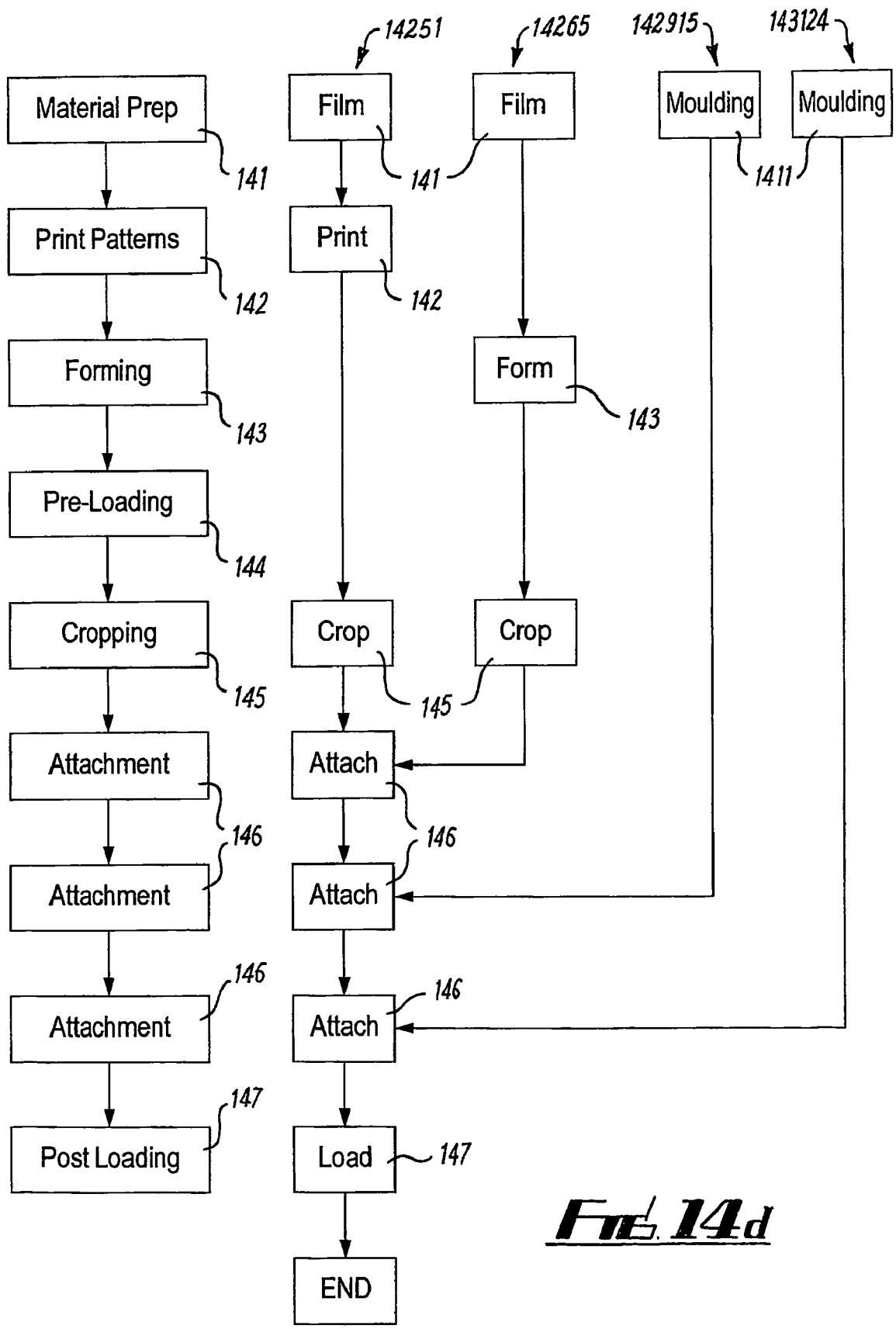

These steps 141 to 147 have many possible permutations and FIGS. 14b, 14c and 14d illustrate by way of example, the fabrication sequence of some of the alternative embodiments described within this document.

Figure 19:
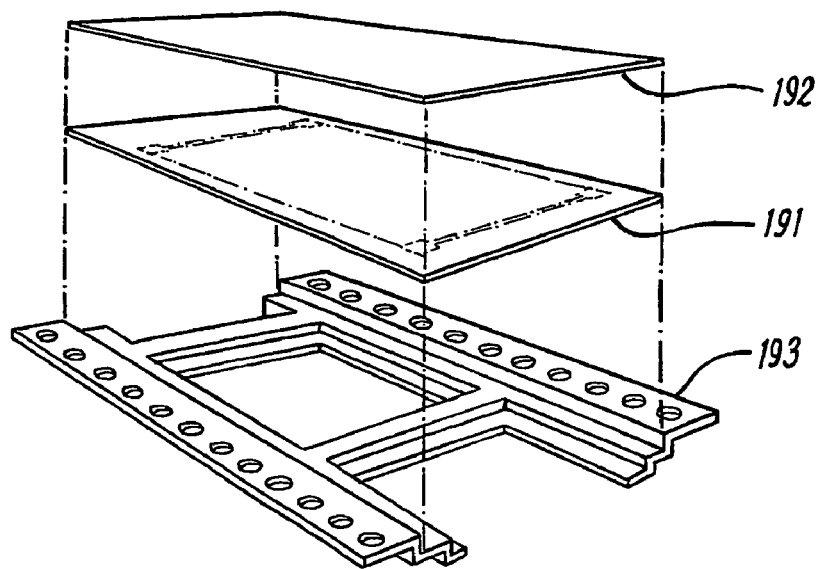
FIG. 19 illustrates in schematic form the components of a planned fabrication scheme of one embodiment.

FIG. 14b shows the general fabrication sequence for the three layer construction method described by FIG. 19 including the fabrication steps 14191, 14192 and 14193 of the substrate 191 sealing layer 192 and carrier layer 193 respectively.

Figure 22:
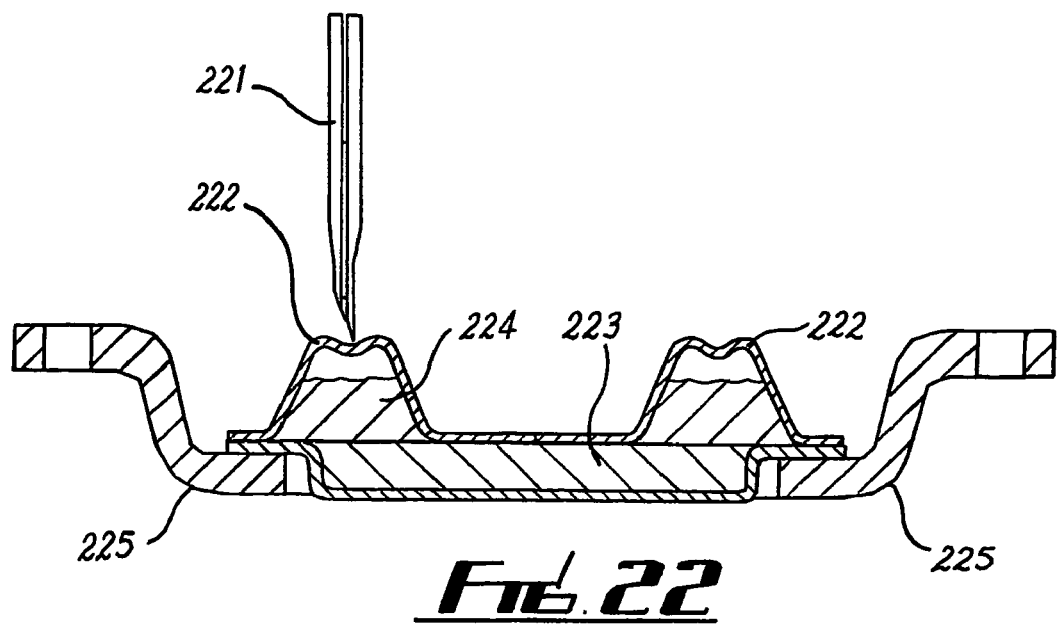
FIG. 22 illustrates in schematic form reservoir fabrication showing the option of sample loading through penetration of a cover seal.

FIG. 14c shows the general fabrication sequence for the three layer construction method described by FIG. 22, including the fabrication steps 14221, 14222 and 14225 of the substrate 221 sealing layer 222 and carrier layer 225 respectively.

FIG. 14d shows the general fabrication sequence for the construction method described by FIG. 1b including the fabrication steps 14251, 14265, 142915 and 143124 of the substrate 251 process layer 265, exoskeleton 2915 and sealing caps 3124 respectively.

In each of FIGS. 14a to 14d, the material preparation step 141 is a film forming step, except for the exoskeleton and sealing cap material preparation 1411, which is a moulding step.

Figure 15:
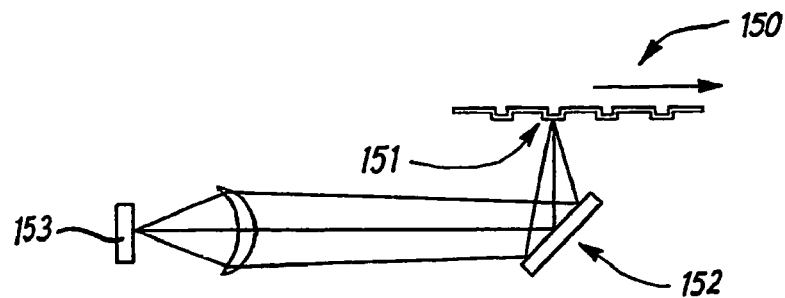
FIGS. 15 and 16 illustrate arrangements of scanning the optical detectors for scanning the apparatus.

With reference to FIG. 15, the moving apparatus 150 with indexing patterns that are permeation (for separation) indents 151, can provide the scanning function of a scanning optical detector with fixed optics 152 and a fixed line scan Charged Coupled Device (CCD) detector 153.

Figure 16:
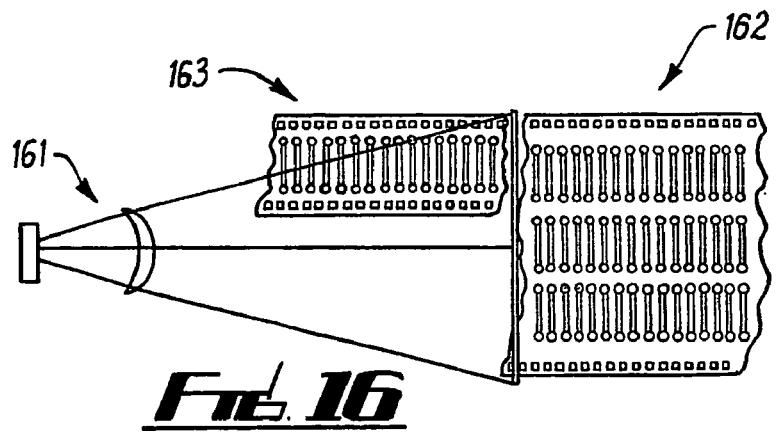

Additionally, with reference to FIG. 16, when this fixed scanning system 161 is configured to suit a chosen width of tape apparatus 162 (e.g. 100 mm, shown in plan view, not to scale) or multiple transverse separation layers, then it can also image capture, without modification, any other tape apparatus which is of lesser width 163 (e.g.50 mm or 20 mm), thus providing the advantage of a detection system with flexibility in the handling of different widths of substrate.

Additionally, where the substrate is configured to have more than one discrete permeation layer in a transverse line across the substrate, each of these more than one discrete permeation layers can be imaged simultaneously.

In the emerging field of biological micro-arrays, the processing substrates are typically comprised of a rigid transparent material (e.g. a glass slide) and whereby bio-material is deposited locally on a rectangular grid whose pitch may be in the range of 50 um to 2 mm. The present invention provides the advantage that it is equally suitable as a substrate for micro-array fabrication but offers the benefit of having low fabrication cost and a capability for continuous processing due to the flexible nature of the apparatus in its form as a continuous tape.

Figure 17:
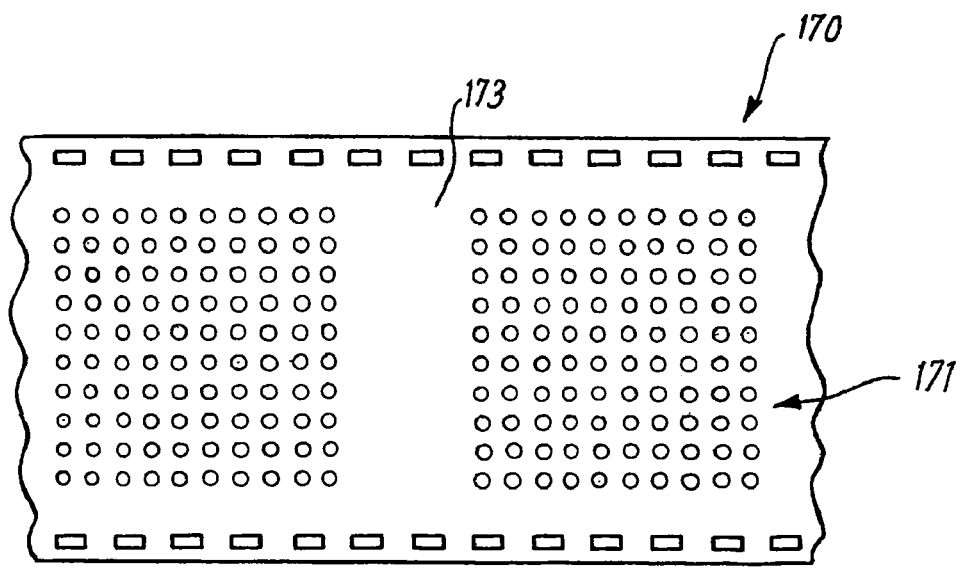
FIG. 17 illustrates plan and elevation views of a micro-array configuration of the apparatus.
Figure 18A:
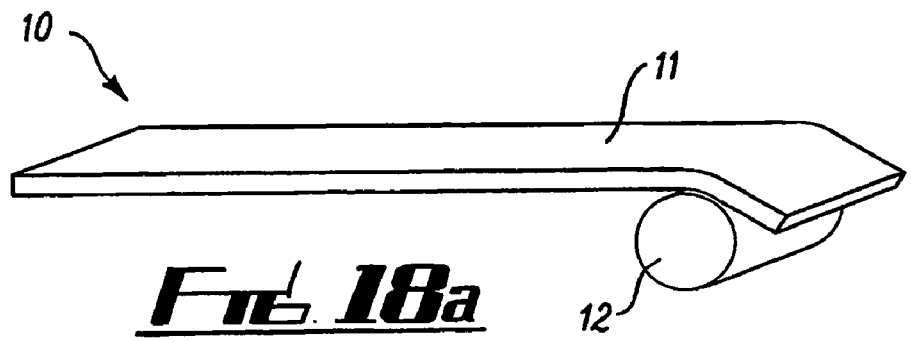
FIG. 18 illustrates in schematic form non-rigid apparatuses in accordance with the present invention.
Figure 18B:
Figure 18C:
Figure 18D:
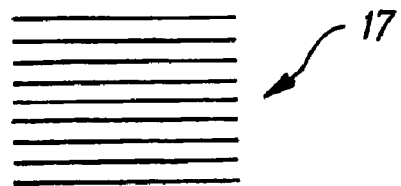
Figure 18E:
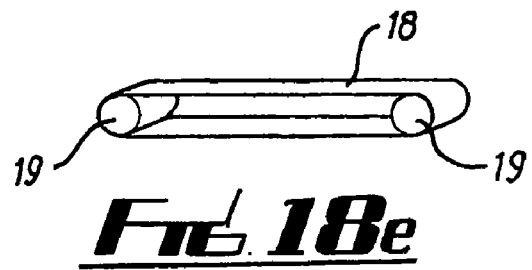

With reference to FIG. 17, the apparatus is illustrated schematically 170 in plan and side views configured to locate each element of a micro-array 171 in a shallow well or dimple 172, on a tape 173, thereby allowing a reduced risk of cross contamination between adjacent elements.

The apparatus is thus configured to provide an improved degree of containment for any reaction process which is specified to take place on that micro-array element and that this improved degree of containment can allow operations of mixing, stirring or agitation which would not be achievable with planar micro-arrays.

The apparatus is configured such that this shallow well has a thin wall section 174 (e.g. 0.1 mm, compared to a glass slide of typically 1 to 3 mm) that enables the efficient coupling of a conductive heating element 175 (for example a peltier device or similar) to the well for the purpose of, for example, hybridisation of a DNA sample at a temperature in the range of, for example, 60 to 80 degrees centigrade.

This thin wall section can readily be transparent and that this enables the efficient coupling of an optical system 175 to detect the bio-reaction state of any element on the microarray.

The apparatus can also have different regions functionalised for the attachment of chemical or biological moieties such as affinity tags or biological probes. Within a microfluidic channel, there can be micro-zones incorporating reactive groups for highly specific functions, e.g. an affinity tag such as a streptavidin coated zone.

With reference to FIG. 18, an apparatus 10 according to the present invention is shown. The apparatus 11 is non-rigid and is shown as being bent, by the apparatus being conformed to the surface of a roller 12.

The apparatus is non-rigid in that it is pliant, unlike rigid apparatuses known in the prior art that are made of at least one layer of hard plastic or glass or silicon, or where the composite apparatus is rigid. On deformation of the apparatus according to the present invention, the apparatus can return to its original shape (i.e. flat) after deformation. The apparatus may have a bend radius approaching zero.

The apparatus is a tape in that it is substantially longer than it is wide in its larger two dimensions. Hence it is a substantially continuous, narrow, flexible strip. The tape 13 may be arranged in a reel-to-reel arrangement between reels or rollers 14 and 15.

With extreme deformation, the apparatus may be folded and remain folded. This may be facilitated by using perforations or indentations to weaken the fold line. Thus the apparatus may be folded into a fanfold arrangement 16 for storage, dispensing and processing.

The tape can also be separated into short discrete sections 17. The separation may be performed by guillotining or tearing across perforations or indentations in the tape.

A continuous strip of tape 18 may be arranged around rollers 19 into a conveyor belt arrangement. A twist in the tape would provide a Moebius strip arrangement.

The apparatus may be formed from a polymer film, that is a thermoplastic polymer film, thermosettable polymer film, elastomeric polymer film or hybrid compositions of each of these films.

In another embodiment, the tape comprises three primary construction elements as illustrated with reference to FIG. 19. The tape incorporates a thin polymer substrate 191 that is formed to create indented wells, channels and junctions which can be configured to create a wide range of microfluidic geometries. This substrate may optionally incorporate one or more surface coating layers on the processing side of the substrate and these layer(s) may fully cover the substrate surface or be confined to local areas of the substrate. The substrate may incorporate liquid or solid chemicals within the well or channel areas of the substrate.

The substrate and its chemical contents may be protected by the attachment of a cover seal 192 membrane. The combined substrate and cover seal will be attached to a carrier layer 193 whose function is to protect the substrate from mechanical stress or damage during handling, shipment, storage or end user processing. The tape may be a one time use consumable item.

The tape assembly employs construction materials, fabrication techniques and packaging methods that ensure that the tape will function reliably at its final point of use. The tape will therefore be unaffected by:

Automated and manual handling processes prior to shipment packaging (factory);
Automated and manual handling processes at the point of use (end user);
Shipment transport (protected by secondary packaging);
Transport temperatures of −40 C to +70 C (up to 24 hours);
Storage temperatures of 0 C. to +40 C. (up to 12 months);
Relative humidity in range 10% to 90% (transport and storage); and
Atmospheric pressure (air cargo).

The substrate comprises a thin polymer membrane with a thickness of 50 um preferred, but 125 um for some applications. The thickness may be selected to match available commercial film grades.

The substrate has:
Forming radius equal to thickness without stress cracking;
Feature width to depth ratio, typically in range 2:1 to 1:1;
Uniform (consistent) draw during forming.

Thermal assist during (or prior to) forming is desirable. Forming may be:
1) high pressure in range 1 bar to 200 bar
2) Vacuum
3) high pressure with vacuum assistance
All of these may benefit from a pre-heating cycle.
Desirable features of the substrate include:
stable after forming (having no shape memory effects);
Flexible, non rigid, non brittle;
Abrasion Resistant;
Punchable, to create optional holes for mechanical indexing;
Penetratable by probe (e.g. for liquid delivery or for electrical probing);
High optical clarity;
Adaptable via suitable surface modification to minimise static charge or to locally influence hydrophilic/hydrophobic surface characteristics;
Chemical Resistance to Aqueous solutions
Analyte material loaded in the substrate channels typically comprised of Agarose or Polyacrylamide,;
Provide bio-compatible surface (e.g. DNA, proteins, cells, bacteria etc);
Avoid leeching of metals, anti-oxidants and stabilisers;
Capable of receiving a heat sealable cover layer e.g. polyester/polyethylene cover layer; and
Printable with ink, stroke widths down to 0.1 mm.
Auxiliary coatings or deposited layers on the substrate include:
Local conductive tracking;
Local hydrophobic coatings (e.g. PTFE);
Local hydrophilic coatings (eg titanium oxide); and
Bio-compatible coatings (e.g. parylene).

The seal 192 may be a single or composite layer but a dual composite construction may be beneficial in that the outer layer can be specified to resist the thermal affects of the heat sealing tool whereas the inner layer is able to melt and create a seal without putting the integrity of the membrane at risk. Properties of the seal layer include:
Seal Thickness: Typically in range 10 um to 50 um;
Chemical Resistance: As per substrate above;
Optical : As per substrate above;
It is preferred that the seal be suitable for penetration by a probe (typically 0.5-1 mm diameter) e.g. for liquid delivery or for electrical probing. A self healing or re-sealable penetration hole is preferred.

Pre-forming of the seal (schematically as in FIGS. 22 and 23) is optional to enhance rigidity of the sealing layer during penetration and to provide the necessary space within the tape for processing materials.

The carrier layer 193 can comply with EIA-481-B (Electronic Industries Alliance), the standard for "Embossed carrier Taping" for automated component handling in the electronic industries. A preferred material is either black or translucent polystyrene, preferred thickness is in the range 100 um to 300 um. This layer will be formed prior to assembly of the substrate/cover such that the substrate/cover will be contained within a recessed channel in the carrier tape and thereby avoid contact with any other surfaces during manufacture or distribution (e.g. in a reel), or at point of use.

The primary functions of the carrier layer are a) to provide a mechanically robust carrier for the more fragile substrate/cover layers b) incorporate punched holes which provide a means of transport drive for the tape c) incorporate registration features which align the substrate/cover layer with the punched drive holes d) incorporate apertures which allow the channels in the substrate to be visible from underneath the tape.

Figure 20:
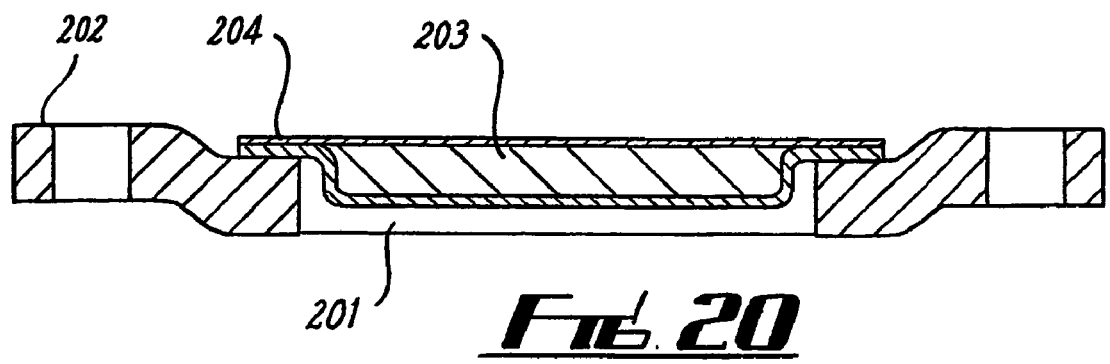
FIG. 20 illustrates in schematic form a compact fabrication option.

With reference to FIG. 20, which is a section across the width of the tape, not to scale, a 50 um thick microfluidic substrate 201 formed up to 250 um deep, is contained within the 300 um thickness of the carrier 202 thus affording it protection. The substrate has analyte 203 and is capped with the seal 204.

Figure 21:
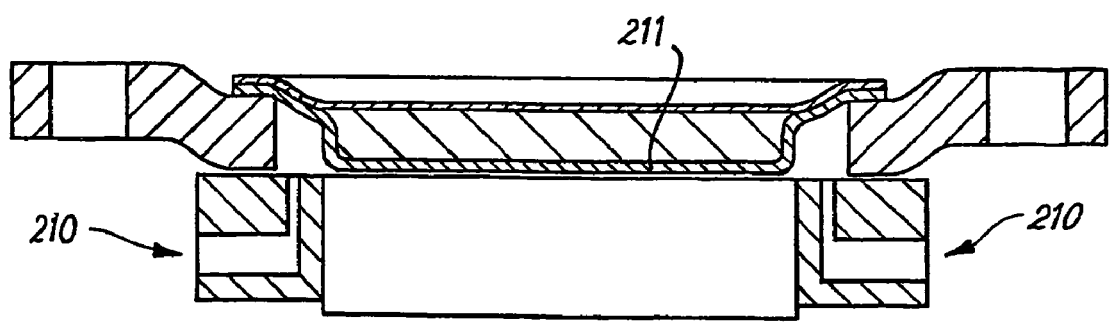
FIG. 21 illustrates in schematic form an operating mode using a vacuum suction onto a scanner or a heating/cooling plate.

With reference to FIG. 21, a negative pressure (vacuum) is applied to the two ports 210 that distorts the substrate onto a tool 211 such as a viewing window of a scanner or a heating/cooling plate.

With reference to FIG. 22, a sample loading probe 221 is positioned ready to penetrate a reservoir in the pre-formed cover seal 222 (that is dimpled for ease of insertion). The substrate contains analyte 223 and the reservoir contains electrolyte 224.

Figure 23:
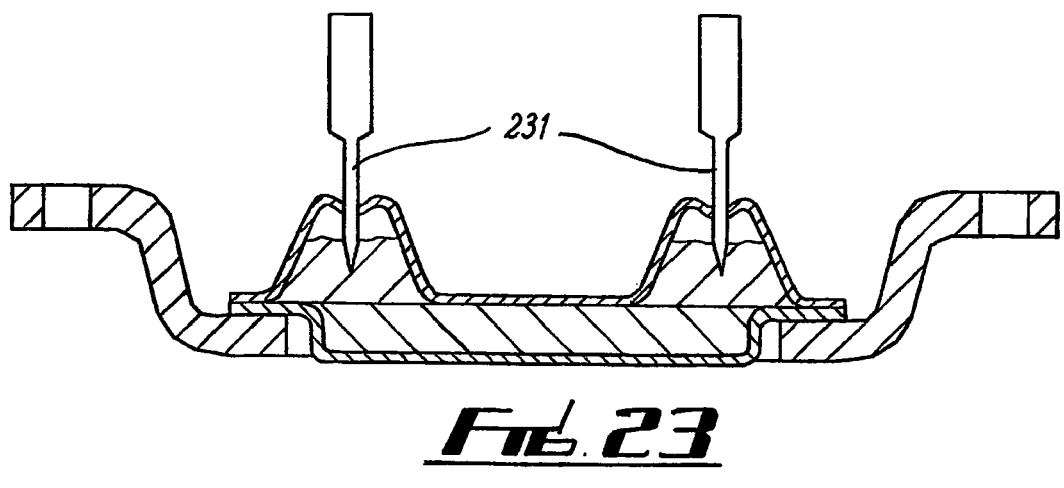
FIG. 23 illustrates in schematic form reservoir fabrication showing the option of electrical probe penetration of a cover seal.

With reference to FIG. 23, electrokinesis 231 probes are shown penetrating the reservoirs.

Figure 24:
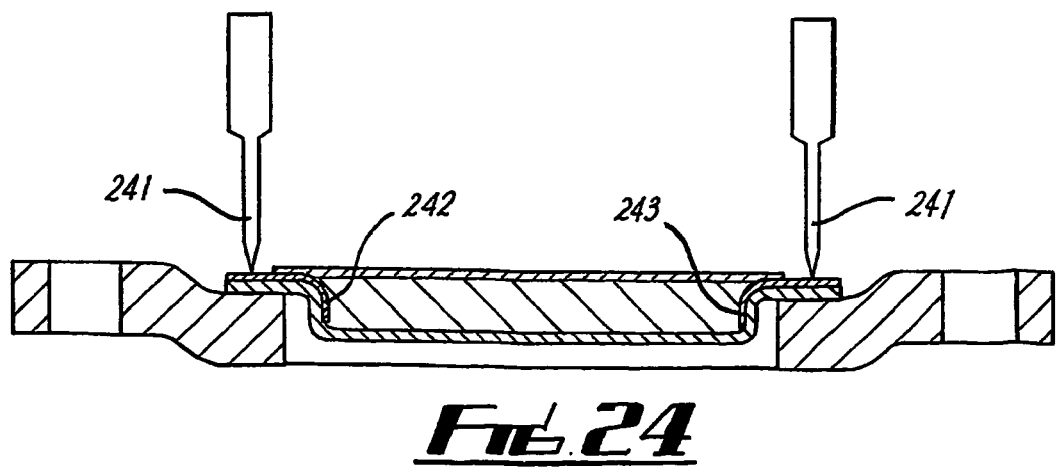
FIG. 24 illustrates in schematic form an alternative electrical probe option.

With reference to FIG. 24, probes 241 external to the "wet chemistry" zone are shown connecting to conductive layers on the substrate that are an anode 242 and a cathode 243.

For the preferred embodiment, a single segment of tape will be described below, comprising the means of processing one discrete test sample of bio-material such as DNA.

Figure 25:
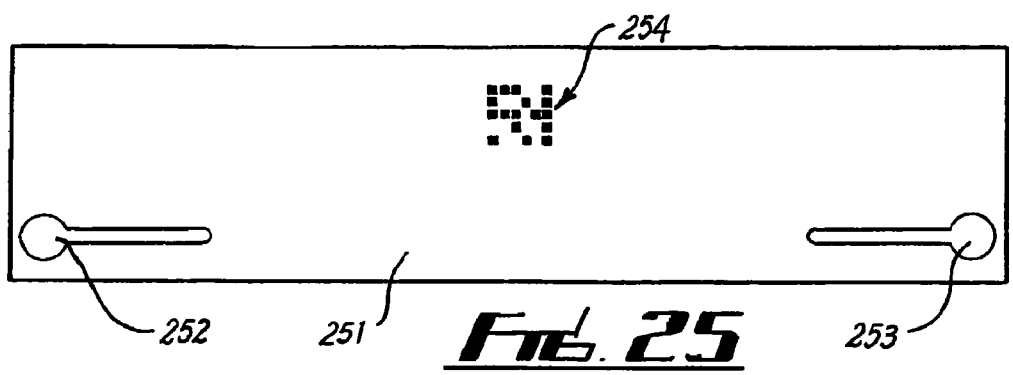
FIG. 25 illustrates in schematic form a supporting layer of one segment of a tape after preparatory printing.

FIG. 25 shows a supporting layer 251 comprises a thin flat optically clear film of either polycarbonate, polyester, polystyrene, poly methyl methacrylate, or other co-polymers of these materials. This film will typically be 125 um thick but other thicknesses in the range 25 um to 1000 um may be used. This Layer has a pattern of conductive tracks 252 and 253 applied by screen printing or laser printing or ink jet printing as well as a pattern 254 which can be machine read to indicate the identity of that segment.

Figure 26:
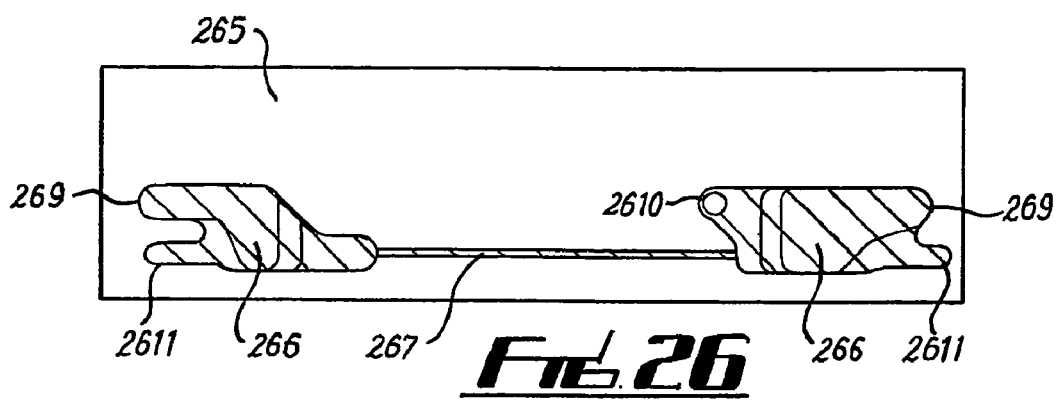
FIG. 26 illustrates in schematic form a formed pattern layer after forming.

FIG. 26 shows a formed patterned layer 265 comprising a thin film of either polycarbonate, polyester, polystyrene, polyethylene, polymethyl methacrylate, polypropylene or other co-polymers of these materials. This film will be typically 50 um thick but other thicknesses in the range 10 um to 200 um may be used. This material need not be optically transparent and some advantage may be gained by having it translucent or opaque; translucency offers a means of back-lighting scatter (opposite side from the optical supporting layer) which may be used for illuminating and capturing an image of the tape processes; opaqueness offers the possibility of using a reflected front-lighting source.

High pressure thermoforming is preferably used to create formed cavities 266, connecting channels 267, optional side channels 268, primary access ports 269 and secondary optional access ports 2610. Shallow channels 2611 provide entry slots for the conductive tracks 252, 253. Typical relative depths of these formed features is illustrated in typical section FIG. 31.

Figure 27:
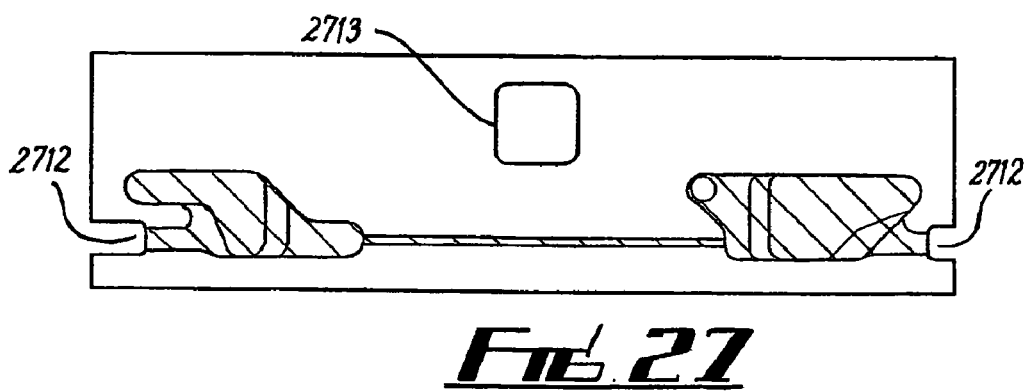
FIG. 27 illustrates in schematic form a formed pattern layer after a blanking operation.

FIG. 27 shows a further preparative step in manufacturing the formed patterned layer whereby a knifing or blanking process is used to cut apertures or slots in the film. Apertures 2712 provide the access entry slots for the conductive tracks 252, 253. Aperture 2713 ensures that the code mark 254 is not obscured by any translucency or opaqueness in the film 265.

Figure 28:
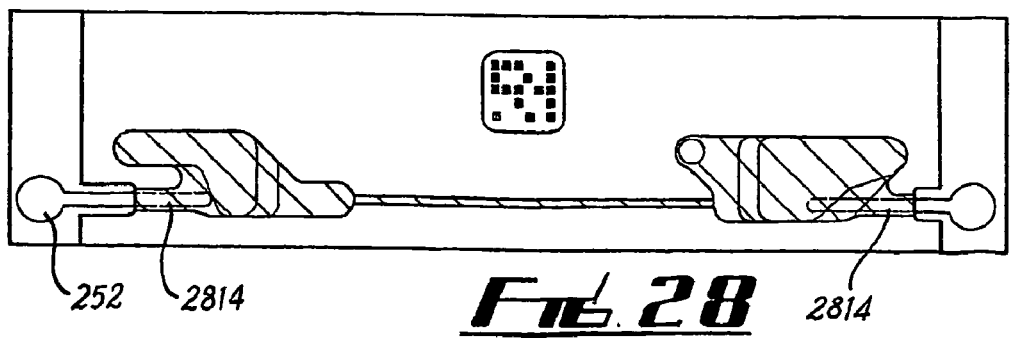
FIG. 28 illustrates in schematic form a formed pattern layer assembled to the supporting layer.

FIG. 28 shows layer 251 and layer 265 assembled together. This will be effected by either a heat sealing or an adhesive process or both, to ensure that the two layers achieve a tight seal around the profile of the various patterned recesses 266, 267, 2611 etc. in Layer 265. Heat sealing can be achieved by the contact surface material of Layer 265 comprising a thin layer of low melting point polymer such as poly-ethylene; alternatively adhesive bonding can comprise the use of commercial cyano-acrylate or, in the case of sealing zones 2814, a commercial silicone rubber compound may be used.

FIG. 29 shows an exoskeleton component 2915 whose purpose is to protect layer 265 as well as providing rigid access ports 2916, 2917 for loading and unloading the tape. Apertures 2918 protect the cavities 266 and an aperture 2919 protects the channel 267.

The exoskeleton material is preferably a rigid polymer such as polycarbonate, ABS, polyester, polystyrene, polyethylene, polymethyl methacrylate, polypropylene or other co-polymers of these materials. This exoskeleton will be typically 1.0 mm thick but other thicknesses in the range 0.5 mm to 3 mm may be used.

FIG. 30 shows the rigid exoskeleton 2915 affixed to the layer 251 plus layer 265 assembly. This may be by adhesive bonding or by incorporating protrusions in the exoskeleton 2915 which will snap fit into corresponding apertures in the supporting layer 251. Where the Layer 265 adjoins an access port on the exoskeleton 2915, for example, at cavity locations 3021, an adhesive layer, preferably a commercial silicone rubber compound, will ensure intimate local contact between Layer 265 and exoskeleton 2915.

FIG. 31 shows a section 3100 through the assembly 3101 along the line "D" to "D". Depths are exaggerated in this figure for clarity, but a typical overall height of the exoskeleton is 1 mm. This cross section shows that cavities 266 are raised to the height of the exoskeleton, cavities 269 are raised to a lesser extent (typically 0.5 mm) and the channel 267 has a low profile (typically 50 to 200 um deep). A conductive strip 253 (typically 20 to 50 um thick) is shown entering a cavity 256. Sealing plugs 3124 are shown at the access port locations. These sealing plugs will comprise compliant polymer, preferably an elastomer such as polyurethane or silicone rubber. These plugs will incorporate a feature allowing removal and replacement by a simple hand tool or, for continuous unattended operation, allow automated removal and replacement. Note also feature 3123 which is a tapered section of cavity forming a smooth transition between the cavity 266 and the channel 267.

Figure 32:
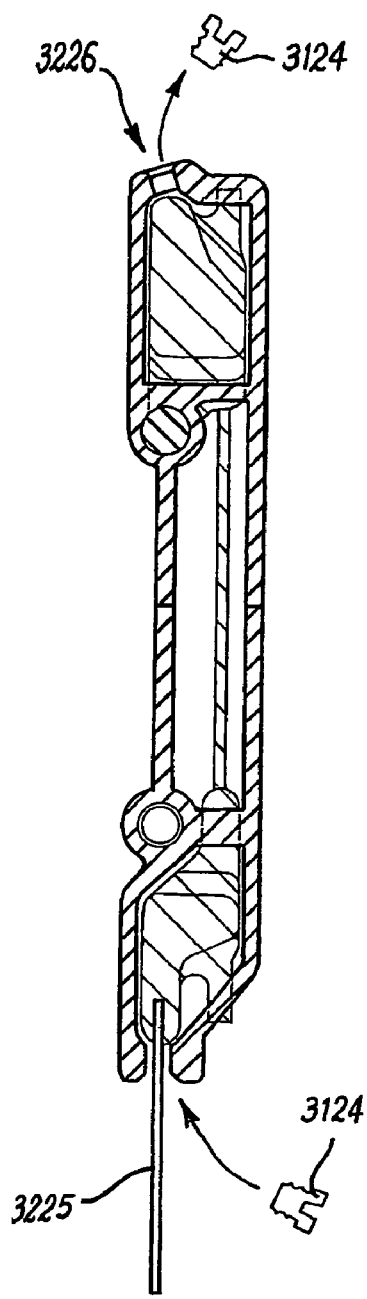
FIG. 32 illustrates in schematic form loading of electrolyte during manufacture.

FIG. 32 shows a method of loading liquid electrolyte (for example 2 mM Tris, 2 mM Acetate, 0.5 mM EDTA) by accessing a probe 3225 into an end cavity. Locations 3226 may be vented and sealed (plugs 3124) as part of the filling process. Note that the micro-scale of the penetration points will allow surface tension to prevent unwarranted leakage while the sealing caps are applied.

Figure 33:
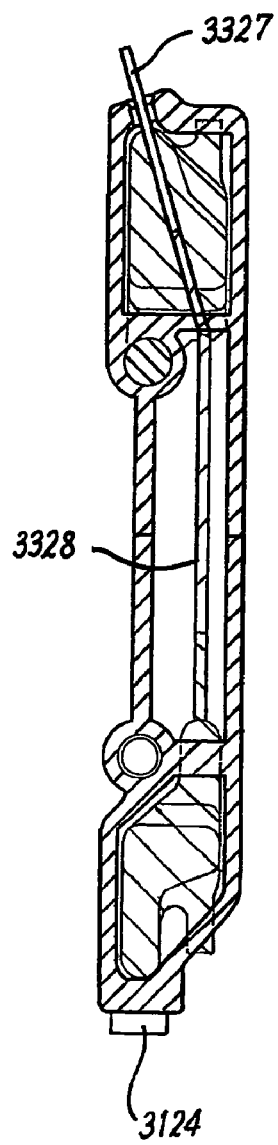
FIG. 33 illustrates in schematic form loading of analyte during manufacture.

FIG. 33 shows a method of pre-loading a column of gel 3328 at the point of manufacture using a loading probe 3327. The gel is loaded as a pre-determined dispensed volume from the elution cavity end of the test segment. The gel is preloaded with a fluorescing marker dye.

The test segment has now been pre-loaded ready for use, and will be shipped in this condition to the point of use. The only "wet chemistry" at the point of use is to load the test sample for analysis.

Figure 34:
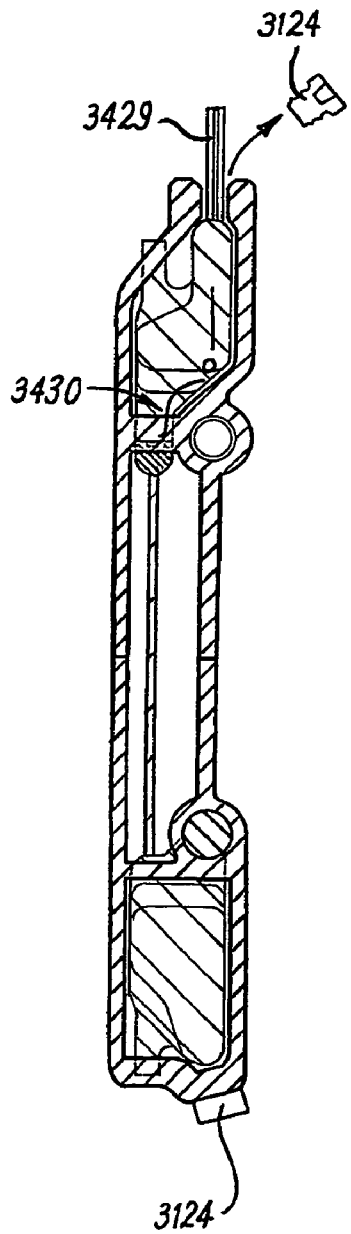
FIG. 34 illustrates in schematic form loading of a test sample at the point of use.

FIG. 34 shows a loading probe 3429 penetrating through the top loading port of the exoskeleton at the point of use. The corresponding cap 3124 may be discarded or replaced depending on whether the tape is required to be archived after use. The test sample 3430 will be prepared in a solution which is denser than the surrounding electrolyte in the tape cavity, for example, a solution of sucrose will ensure that the test sample will flow under gravity into the tapered channel and gather right at the top of the gel column.

The exoskeleton incorporates access ports which can be oriented longitudinally (e.g. port no. 3431) or perpendicularly (e.g. port no. 3432). Optionally port 3432 can be used to vent any unwanted build up of gas in the lower cavity.

These fabrication methods can create features which provide a wide range of processing options at the point of use.

Figure 35:
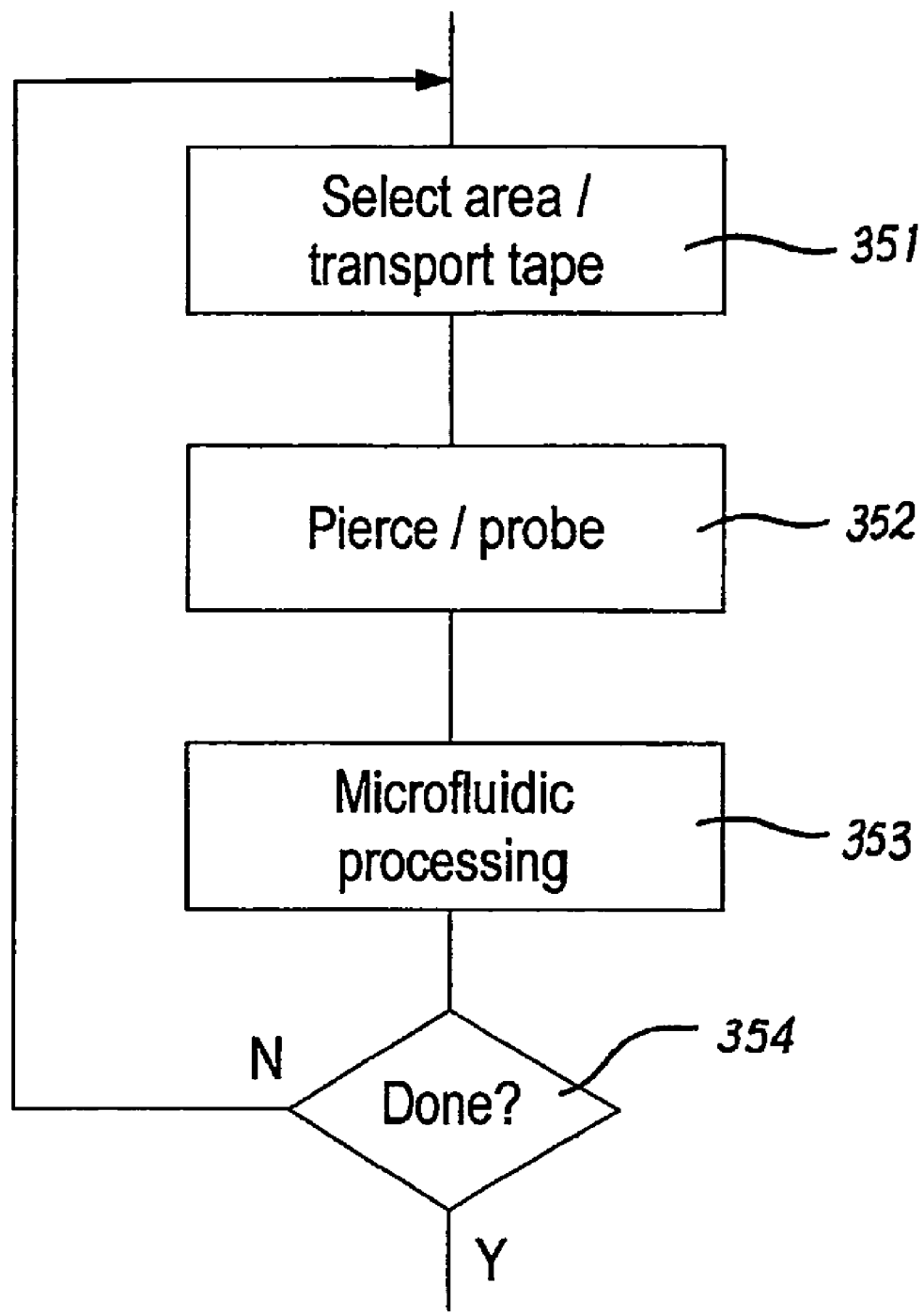
FIG. 35 illustrates in a flowchart of automated processing using the fabricated tape.

With reference to FIG. 35, the automated processing has the steps of transporting the tape and selecting an area for processing 351, piercing the apparatus with a probe or probing the apparatus 352, and performing microfluidic processing 353 at the selected area, then repeating 354 the above steps until processing of the reel of tape is complete.

During these steps the fabricated apparatus with its optional preloaded processing materials may be deformed in order to cause dynamic processing. The apparatus may be deformed by bending, flexing, folding, twisting, conforming to a rigid surface, mechanical deformation, deformation by applying a sound pressure, deformation by applying a liquid pressure, and deformation by applying a gas pressure. Optionally the deformation can result in the bringing of a part of the apparatus back into contact with another part of itself or with another apparatus. The deformation may move part of the apparatus into a position for processing, including being in contact with a processing tool. The deformation of the apparatus results in dynamic processing that includes pumping, filling, pouring, pressurising, mixing, dispensing, aspirating, separating, combining, heating and cooling.

Apparatuses that include impermeable membranes facilitate further novel processing methods that involve the impermeable membrane. The membrane may be pierced by one or more probes. These probes may be pipettes. Conducting probes that have pierced the membrane may provide an electrical potential, and used for passing an electric current through the conducting probe into a conducting medium.

Optionally a grid of probes are mounted on a discrete carrier or a continuous carrier that can be indexed or replaced, such that another set of probes can be used after the first set has worn out.

The grid of probes may be configured such that each probe is separately addressable and each probe may have a separate voltage applied in order to progressively move the processing material through processing elements, such as indented troughs and permeation layers in the apparatus, after the grid of probes has penetrated or contacted a corresponding grid of impermeable membranes. This arrangement can be used to move process materials through permeation layers for molecular separation. The controlled and progressive switching of voltages on the grid of probes can be used to split processing material into more than one separate processing path through more than one separate processing elements. These split process materials may be further combined or different process materials may be combined at the junctions of paths through the apparatus. In this way, the grid of electrical probes can be configured to apply voltages that cause a multi-dimensional separation of molecules, e.g. polypeptide or protein molecules.

If the probes are pipettes, processing materials may be introduced into the apparatus through the impermeable membranes that have been penetrated or processing materials removed from within the apparatus. An array of pipettes compatible with 96, 192, 384, 1536 or 3456 well assay plates can be matched to an array of commensurately spaced impermeable membranes for penetration by the array of pipettes. Probes that penetrate or touch the surface of a membrane can cause processing to be performed, such as pumping, filling, pouring, pressurising, mixing, dispensing, aspirating, separating, combining, heating, cooling, movement by electrokinesis, movement by electrokinesis, movement by the molecular entrapment method of molecular tweezers, acoustic tweezers and bio-molecular motor principles.

An apparatus in the form of a tape may be transported through processing equipment and handling equipment by friction of, for example, rollers in contact with the apparatus or by pinions inserted into indents or perforations in the apparatus in a similar manner to the handling of photographic or cine film. Alternative methods of moving the tape include sliding drawers and walking beams. Moving the apparatus with electromagnetic fields and induction within the apparatus or moving using air or fluid pressure applied to the apparatus are also possible.

The position of the apparatus in response to movement is detected by measurement of indexing patterns. After movement dynamic processing can be performed and then further repeated movement and dynamic processing steps can be performed in a continuous fashion as the continuous tape is indexed through the processing equipment.

In conclusion, we present the advantages of the present invention.

A significant and long-established traditional art for some of the kinds of bio-molecular separation described herein is commonly referred to as "slab gel electrophoresis". The demands in material usage, process time, operator time and workspace for this process are recognised by those with even minor experience of this art. The procedure commonly employs manual preparation of gels involving mixing, heating and casting steps. Although the method can now employ pre-cast gels to provide some degree of improvement, the overall process remains manually intensive and inefficient.

In contrast, the present invention offers significant advantages, by miniaturising all the elements of this traditional process and eliminating many of the material preparation and manual processing tasks.

While the traditional processes remain in common use, new art is emerging which includes miniaturised bio-analysis systems employing chip-scale technology, micro-fluidics, and semiconductor fabrication techniques.

The present invention provides advantages over both traditional and emerging techniques.

The present invention provides very significant savings in materials, time and workspace over traditional gel electrophoresis methods.

The present invention provides an adaptable platform for a very wide range of bio-analysis processes (not just gel electrophoresis) and employs geometric patterning, tooling methods and fabrication methods which are much less complex than other emerging micro-fluidic or chip scale techniques. This allows rapid and cost effective production of multiple versions of tape to match the range of applications anticipated.

The present invention allows bio-sample processing in a range from one single simple test up to highly parallel and multiple complex tests in an uninterrupted continuous serial or parallel mode. The former is attractive to small research laboratories, many quality control laboratories, and point of care clinics. The latter is attractive to high throughput processing laboratories. A combination of these processing methods is attractive to public health hospitals and clinics whose demand can fluctuate significantly. This range of capability is provided in one single effective and efficient platform regardless of usage patterns.

The present invention configures processing elements on a highly flexible substrate and enables a versatile range of substrate indexing patterns and transport methods to be utilised as described.

Additionally, these transport methods provide the advantage of allowing the use of non complex, compact, low cost optical scanning means by the embodiment of a fixed position transverse optical line-scanning system whose focal plane is along a line across the width of the substrate. The scanning function is provided by the (already provided) indexing motion of the substrate.

This highly flexible substrate also enables the other described features and advantages which result from bending, folding, twisting, flexing and deforming its geometry.

The substrate flexibility also allows it to be penetrable by probes for the purposes of processing material delivery or removal, electrical connection and process tooling introduction.

Additionally this flexible substrate is suitable for affixing a secondary impermeable membrane which is also readily penetrable by suitable probes for the purposes of processing material delivery or removal, electrical connection, process tooling introduction.

The penetrable substrate and penetrable membrane provides a processing system which can be fully enclosed and which can provide some processing materials pre-loaded within the system. This minimises preparation, avoids spillage, avoids the need for cleaning or flushing procedures and simplifies waste disposal.

Alternatively, a stereo-lithographic method is described to fabricate the substrate and the impermeable membrane in one homogenous material with the advantage that this simplifies the means of construction.

Alternatively, a selective laser sintering method is described to fabricate the substrate and the impermeable membrane in a single fabrication process again with the advantage that this simplifies the means of construction.

The present invention employs one generic material type in its construction (polymer) and avoids the significant use of glass, silicon or metal in its fabrication. This simplifies the waste disposal methods after bio-processing is complete.

The fabrication techniques described provide a wide range of substrate geometries. These features can be created by rapid and simple methods of tooling, thus avoiding the long lead times and complexity of other miniaturised bio-processing systems.

The present invention has the advantage that these rapid and simple fabrication techniques correspond to processing elements whose dimensional accuracy is less critical than those of chip scale devices. A corresponding advantage is that this is achieved without sacrifice to the overall device size because the device size, in the current state of the art, is determined by the practicalities of the size of the sample loading wells and not by the processing element sizes.

The present invention can be enhanced by pre-printing processing materials onto a planar plastic film substrate using commercially available printing methods and then by deforming that substrate in a non planar fashion such that the pre-printed material deforms into a desired shape or position and such that, for example, a pre-printed permeation layer can subsequently (after forming of the substrate) be hydrated into its gelatinous phase. Related printing and forming methods are already established in the field of foil manufacture for "in-mould decoration" of plastic injection moulded products (used for cosmetic effect mainly on consumer electronic products), but the present invention provides the scope for adapting these methods into this unconnected field of application.

The flexible substrate is readily available in a range of polymer materials whose optical properties can be matched to available commercial optical systems for detection or imaging of the bio-processing events during system operation.

Further modifications and improvements may be added without departing from the scope of the invention herein described.

The invention claimed is:

1. A microfluidic processing apparatus for use in gel electrophoresis, the apparatus comprising:
   a planar supporting layer comprising a pattern of conductive tracks; and
   a single layer of deformable polymer film comprising a three-dimensional microfluidic processing area that is formed from and extends out of a plane of said single layer of deformable polymer film, said three-dimensional microfluidic processing area comprising at least one cavity, at least one connecting channel and at least one pierceable access zone;
   wherein said microfluidic processing area contains a gel, and
   wherein said pattern of conductive tracks are configured to permit application of an electrical field through said gel.

2. The microfluidic processing apparatus of claim 1 wherein the layer of deformable polymer film is a thin polymer membrane of thickness between 10 μm and 200 μm.

3. The micro fluidic processing apparatus of claim 1 wherein at least one conductive track connects the exterior of said apparatus to the interior of said apparatus.

4. The micro fluidic processing apparatus of claim 3 wherein the conductive tracks are capable of being applied by screen printing, laser printing or ink-jet printing.

5. The microfluidic processing apparatus of claim 1 wherein the access zone is penetrable by a sample loading probe.

6. The microfluidic processing apparatus of claim 1, wherein the layer of deformable polymer film is impermeable to liquid.

7. The microfluidic processing apparatus of claim 1 wherein the three-dimensional microfluidic processing area is capable of being formed using high-pressure thermoforming.

8. The microfluidic processing apparatus of claim 1, further comprising an indexing pattern to track a position of the apparatus during movement.

9. The microfluidic processing apparatus of claim 8 wherein the indexing pattern is a pattern on a surface of the planar supporting layer.

10. The micro fluidic processing apparatus of claim 8 wherein the indexing pattern is embedded within the planar supporting layer.

11. The microfluidic processing apparatus of claim 1 wherein said layer of deformable polymer film is opaque, translucent or colored to provide optical isolation between elements for processing.

12. The microfluidic processing apparatus of claim 1, wherein the supporting layer comprises a thin flat optically clear film.

13. The microfluidic processing apparatus of claim 1, wherein the layer of deformable polymer film further comprises secondary access ports.

14. The microfluidic processing apparatus of claim 1, wherein the supporting layer comprises a thin flat optically clear film, wherein the layer of deformable polymer film is a liquid impermeable thin polymer membrane of thickness between 10 μm and 200 μm, wherein said three-dimensional micro fluidic processing area is capable of being formed using high-pressure thermoforming, wherein the access zone is penetrable by a sample loading probe, wherein said pattern of conductive tracks is capable of being applied by screen printing, laser printing or ink-jet printing and connects the exterior of said apparatus to the interior of said apparatus, wherein an indexing pattern is provided on the surface of the planar supporting layer to track the position of the apparatus during movement, and wherein said layer of deformable polymer film is opaque, translucent or colored to provide optical isolation between elements for processing.

15. The microfluidic processing apparatus of claim 14, wherein the layer of deformable polymer film further comprises secondary access ports.

16. The microfluidic processing apparatus of claim 14, wherein said layer of deformable polymer film is adjacent to said planar supporting layer, and wherein said three-dimensional microfluidic processing area has an internal volume that is defined by said layer of deformable polymer film and said supporting layer.

17. The micro fluidic processing apparatus of claim 1, wherein said layer of deformable polymer film is adjacent to said planar supporting layer, and wherein said three-dimensional micro fluidic processing area has an internal volume that is defined by said layer of deformable polymer film and said supporting layer.

18. The microfluidic processing apparatus of claim 1, wherein said processing apparatus comprises a plurality of said three-dimensional microfluidic processing areas.

19. The microfluidic processing apparatus of claim 1, wherein said planar supporting layer is heat sealed to said single layer of deformable polymer film.

20. The microfluidic processing apparatus of claim 1, wherein at least one of said planar supporting layer and said single layer of deformable polymer film are optically transparent.

21. The microfluidic processing apparatus of claim 20, wherein one of said planar supporting layer and said single layer of deformable polymer film is optically opaque.

* * * * *

UNITED STATES PATENT AND TRADEMARK OFFICE
CERTIFICATE OF CORRECTION

| | | |
|---|---|---|
| PATENT NO. | : 8,124,029 B2 | Page 1 of 1 |
| APPLICATION NO. | : 10/496741 | |
| DATED | : February 28, 2012 | |
| INVENTOR(S) | : Stuart Polwart et al. | |

It is certified that error appears in the above-identified patent and that said Letters Patent is hereby corrected as shown below:

On the Title Page:
Item (56), under "Other Publications", in column 2, line 2, delete "polydimeethylsiloxane" and insert -- polydimethylsiloxane --, therefor.

Signed and Sealed this
Fourth Day of December, 2012

David J. Kappos
*Director of the United States Patent and Trademark Office*